US009233025B2

(12) United States Patent
Spooner

(10) Patent No.: US 9,233,025 B2
(45) Date of Patent: Jan. 12, 2016

(54) LASER APPARATUS AND METHOD FOR REFRACTIVE SURGERY

(76) Inventor: Gregory John Roy Spooner, San Francisco, CA (US)

(*) Notice: Subject to any disclaimer, the term of this patent is extended or adjusted under 35 U.S.C. 154(b) by 1025 days.

(21) Appl. No.: 13/244,446

(22) Filed: Sep. 24, 2011

(65) Prior Publication Data

US 2012/0078240 A1    Mar. 29, 2012

Related U.S. Application Data

(60) Provisional application No. 61/386,507, filed on Sep. 25, 2010.

(51) Int. Cl.
*A61B 18/20* (2006.01)
*A61F 9/008* (2006.01)

(52) U.S. Cl.
CPC ......... *A61F 9/00827* (2013.01); *A61F 9/00836* (2013.01); *A61F 2009/0087* (2013.01); *A61F 2009/0088* (2013.01); *A61F 2009/00846* (2013.01); *A61F 2009/00865* (2013.01); *A61F 2009/00872* (2013.01); *A61F 2009/00882* (2013.01); *A61F 2009/00887* (2013.01); *A61F 2009/00891* (2013.01); *A61F 2009/00895* (2013.01)

(58) Field of Classification Search
CPC   A61F 9/013; A61F 2009/00872; A61F 9/008
USPC ................................. 606/4, 5, 166
See application file for complete search history.

(56) References Cited

U.S. PATENT DOCUMENTS

| 4,665,913 A | 5/1987 | L'Esperance, Jr. |
| 4,840,175 A | 6/1989 | Peyman |
| 4,848,340 A | 7/1989 | Bille |
| 4,907,586 A | 3/1990 | Bille et al. |
| 5,133,726 A | 7/1992 | Ruiz |
| 5,163,934 A | 11/1992 | Munnerlyn |

(Continued)

OTHER PUBLICATIONS

Miguel J. Maldonado. "Undersurface Ablation of the Flap for Laser in Situ Keratomileusis Retreatment". Ophthalmology, vol. 109, No. 8, 1453-1464, Aug. 2002. Published by the American Academy of Ophthalmology.

(Continued)

*Primary Examiner* — William Thomson
*Assistant Examiner* — Jeffrey Lipitz
(74) *Attorney, Agent, or Firm* — MU Patents; Timothy Marc Shropshire

(57) ABSTRACT

An ultrashort pulsed laser instrument is used to perform refractive surgery. The invention operates in ablative and incisional modalities. In the ablative mode, spiral ablation disks (10) consisting of individual laser pulses (40) are produced at high scanning speeds. Ablation profile (11) may be produced in cornea (22) by stacking and arranging multiple ablation disks (10) to produce a specified shape change. Placement of ablation disks (10) is assisted by an optical tracking and control system that compensates for eye motion. A preferred embodiment allows for ablative corrections to be performed on non-planar posterior surface (112) of a laser cut flap affixed to registration platen (120), thereby avoiding exposing the eye interior to high radiant power. Laser cut and contrast agent dyed fiduciary marks (30) may serve as reference features for the optical tracking system. Incisional procedures, such as corneal flaps for LASIK, may also be performed.

12 Claims, 10 Drawing Sheets

(56) References Cited

U.S. PATENT DOCUMENTS

Figure 1:
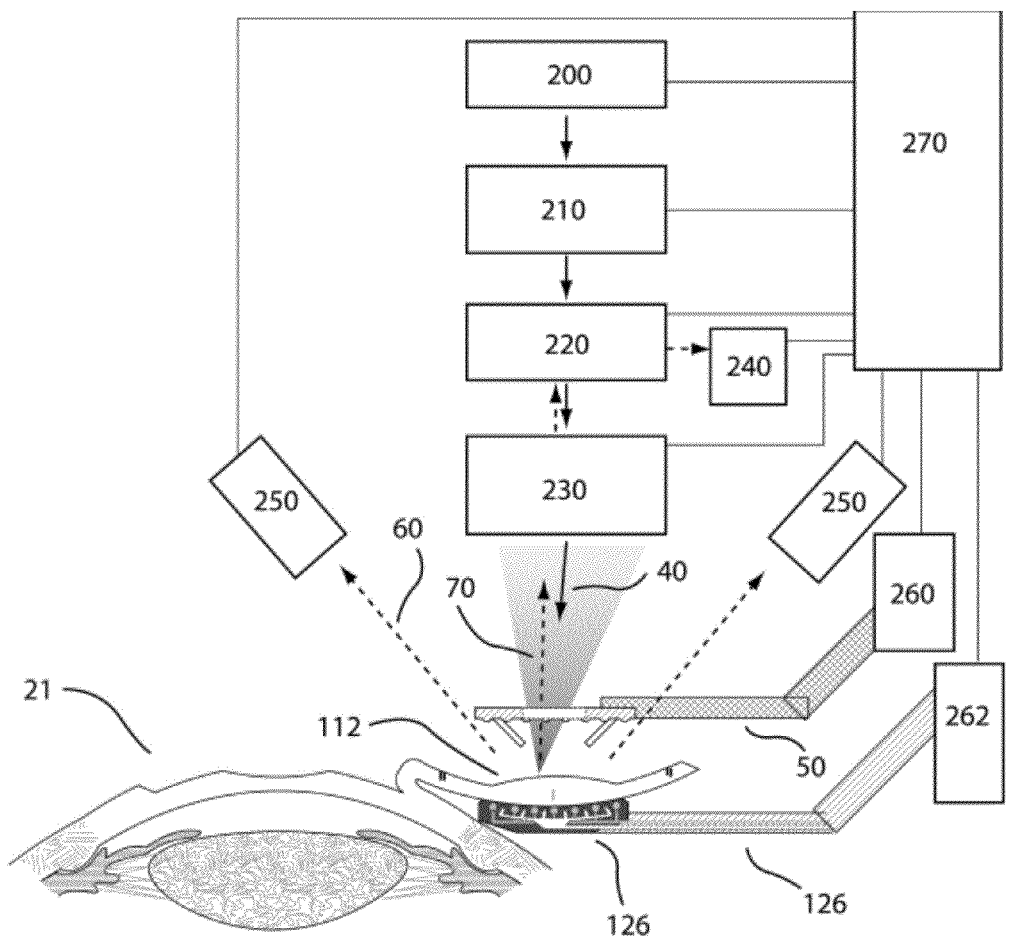

| | | | |
|---|---|---|---|
| 5,350,374 A | 9/1994 | Smith | |
| 5,656,186 A | 8/1997 | Mourou | |
| 5,752,967 A | 5/1998 | Kritzinger | |
| 5,993,438 A | 11/1999 | Juhasz et al. | |
| 6,110,166 A | 8/2000 | Juhasz | |
| 6,254,595 B1 | 7/2001 | Juhasz | |
| 6,579,282 B2 | 6/2003 | Bille | |
| 2001/0053906 A1* | 12/2001 | Odrich et al. | 606/5 |
| 2004/0054356 A1* | 3/2004 | Odrich et al. | 606/4 |
| 2004/0147944 A1* | 7/2004 | LaHaye | 606/166 |
| 2006/0173445 A1* | 8/2006 | Bille | 606/5 |
| 2008/0319428 A1 | 12/2008 | Wiechmann et al. | |

OTHER PUBLICATIONS

Zhen-Yong Zhang, Ren-Yuan Chu, Xing-Tao Zhou, Jin-Hui Dai, Xing-Huai Sun, Matthew R. Hoffman, and Xing-Ru Zhang. "Morphologic and Histopathologic Changes in the Rabbit Cornea Produced by Femtosecond Laser-Assisted Multilayer Intrastromal Ablation" Investigative Ophthalmology & Visual Science, vol. 50, No. 5. May 2009. Published by the Association for Research in Vision and Ophthalmology.

Lance J. Kugler and Ming X. Wang. "Lasers in refractive surgery: history, present, and future". Applied Optics vol. 49, No. 25. Sep. 1, 2010. Published by the Optical Society of America.

Bao-Gui Wang, Iris Riemann, Harald Schubert, Karl-Juergen Halbhuber, Karsten Koenig. "In-vivo intratissue ablation by nanojoule near-infrared femtosecond laser pulses" Cell Tissue Research vol. 328, pp. 515-520, (2007). Published by Springer-Verlag.

Andreas Tunnermann, Thomas Schreiber & Jens Limpert. "Fiber lasers and amplifiers: an ultrafast performance evolution" Applied Optics. vol. 49, No. 25, Sep. 1, 2010. Published by Optical Society of America.

Karl G. Stonecipher, Jon G. Dishler, Teresa S. Ignacio, Perry S. Binder. "Transient light sensitivity after femtosecond laser flap creation: Clinical findings and management" Journal of Cataract and Refractive Surgery. vol. 32, pp. 91-94, Jan. 2006. Published by Elsevier Inc.

Osmond Bruce Hadden, Charles N.J. McGhee, Antony Trevor Morris, Trevor Buchanan Gray, Charles Peter Ring, Adam Stewart John Watson. "Outbreak of diffuse lamellar keratitis caused by marking-pen toxicity" Journal of Cataract and Refractive Surgery. vol. 34, pp. 1121-1124, (2008). Published by Elsevier Inc.

Davson, Hugh. The physiology of the eye. New York: Academic Press. (1972). p. 663.

Takeshi Ide, George D. Kymionis, Ashkan M. Abbey, Sonia H. Yoo, William, W. Culbertson, Terrence P. O'Brien. "Effect of marking pens on femtosecond laser-assisted flap creation" Journal of Cataract and Refractive Surgery. vol. 35, pp. 1087-1090 (2009). Published by Elsevier Inc.

K. D. Solomon, L. E. Fernández De Castro, H. P. Sandoval, J. M. Biber, B. Groat, K. D. Neff, M. S. Ying, J. W. French, E. D. Donnenfeld, R. L. Lindstrom. "LASIK world literature review: quality of life and patient satisfaction," Ophthalmology annual vol. 116, pp. 691-701 (2009). Published by the American Academy of Ophthalmology.

Silvia Schumacher, Michael Fromm, Uwe Oberheide, Georg Gerten, Alfred Wegener, Holger Lubatschowski. "Overview of Commercially Available Femtosecond Lasers in Refractive Surgery" Journal of Refractive Surgery, vol. 24, No. 9, Nov. 2008. Published by the International Society of Refractive Surgery.

M. Wang. Book chapter titled, "Future direction: technological development and treating the problem at its source," from the text "Irregular Astigmatism: Diagnosis and Treatment" M.Wang, ed. (2008), pp. 279-284. Published by Slack, Inc.

M. Wang. "Corneal Topography in the Wavefront Era: a Guide for Clinical Application" (2006). Published by Slack, Inc.

Haft P, Yoo SH, Kymionis GD, Ide T, O'Brien TP, Culbertson WW. "Laser in situ keratomileusis (LASIK) complications with the femtosecond laser" Journal of Refractive Surgery. vol. 25, pp. 979-984 (2009). Published by the International Society of Refractive Surgery.

Yi-Yu Tsai, Sung-Huei Tseng, Jane-Ming Lin. "Comparison of ablation centration in initial and retreatment active eye-tracker-assisted laser in situ keratomileusis and the effect on visual outcome" Journal of Cataract and Refractive Surgery. vol. 30, pp. 1521-1525 (2004). Published by Elsevier Inc.

Daniel X. Hammer, R. Daniel Ferguson, Chad E. Bigelow, Nicusor V. Iftimia, Teoman E. Ustun. "Adaptive optics scanning laser ophthalmoscope for stabilized retinal imaging" Optics Express. vol. 14, No. 8, pp. 3354. Apr. 17, 2006.

Marcella Q. Salomao, Steven E. Wilson. "Femtosecond laser in laser in situ keratomileusis" Journal of Cataract and Refractive Surgery. vol. 36, pp. 1024-1032. (2010) Published by Elsevier Inc.

Gaurav Prakash, Amar Agarwal, Dhivya Ashok Kumar, Soosan Jacob, Athiya Agarwal, Amrita Maity. "Surface Ablation With Iris Recognition and Dynamic Rotational Eye Tracking-based Tissue Saving Treatment With the Technolas 217z Excimer Laser" Journal of Refractive Surgery. (2010) Published by the International Society of Refractive Surgery.

Irmingard M. Neuhann, Barbara A.M. Lege, Markus Bauer, Joerg M. Hassel, Anton Hilger, Thomas F. Neuhann. "Static and Dynamic Rotational Eye Tracking During LASIK Treatment of Myopic Astigmatism With the Zyoptix Laser Platform and Advanced Control Eye Tracker" Journal of Refractive Surgery. vol. 26, No. 1 (2010). Published by the International Society of Refractive Surgery.

George Waring. "One-kilohertz Eye Tracker and Active Intraoperative Torsion Detection in the NIDEK CXIII and Quest Excimer Lasers" Journal of Refractive Surgery. vol. 25 (Suppl) Oct. 2009. Published by the International Society of Refractive Surgery.

Jane-Ming Lin, Wen-Lu Chen, Chun-Chi Chiang, Yi-Yu Tsai. "Ablation Centration After Active Eye Tracker-assisted LASIK and Comparison of Flying-spot and Broad-beam Laser" Journal of Refractive Surgery. vol. 24, pp. 371-373, Apr. 2008.

Michael Mrochen, Maik Kaemmerer, Peter Mierdel, Theo Seiler. "Increased higher-order optical aberrations after laser refractive surgery—A problem of subclinical decentration" Journal of Cataract and Refractive Surgery. vol. 27, pp. 362-369. (2001) Published by Elsevier Inc.

Michael Mrochen, Mostafa Salah Eldine, Maik Kaemmerer, Theo Seiler, Werner Hutz. "Improvement in photorefractive corneal laser surgery results using an active eye-tracking system" Journal of Cataract and Refractive Surgery. vol. 27, pp. 1000-1006. (2001) Published by Elsevier Inc.

"Raydiance Report: Smart Light Applications in the Therapeutic Market" Feb. 5, 2010. White paper web-published by Raydiance, Inc. http://raydiance-inc.com/solutions/industry-applications/medical-therapies.

* cited by examiner

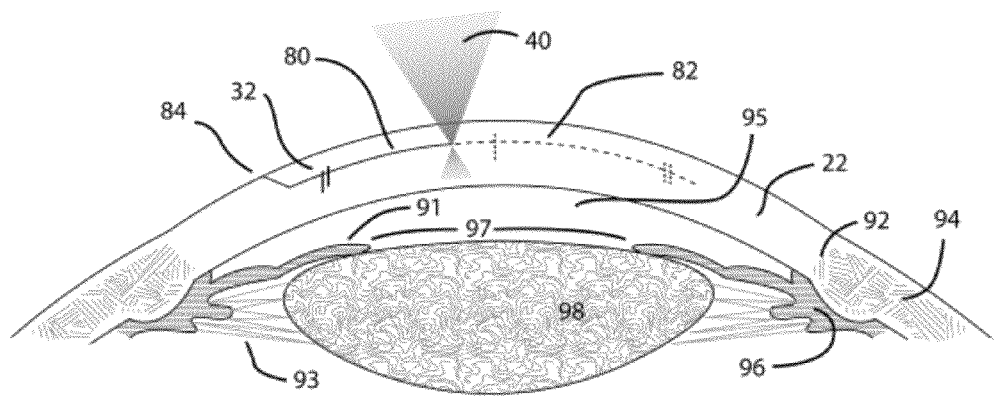
FIG. 8A
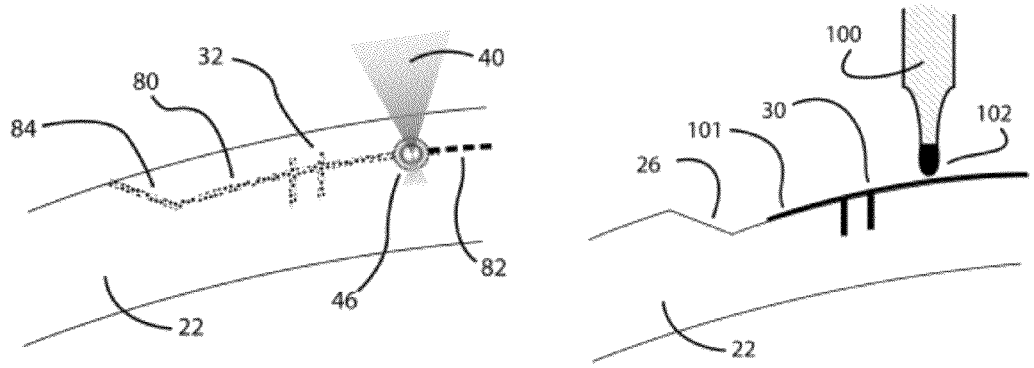
FIG. 8B
FIG. 8C
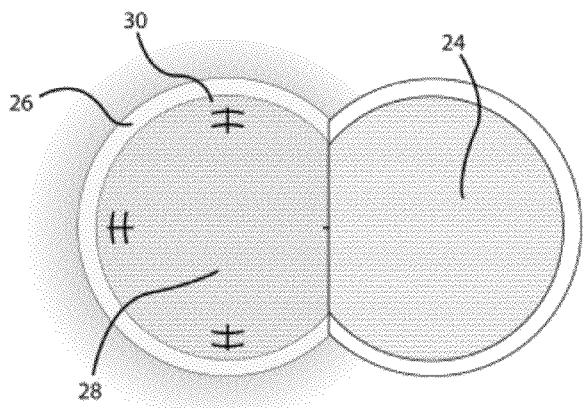
FIG. 8D

LASER APPARATUS AND METHOD FOR REFRACTIVE SURGERY

CROSS-REFERENCE TO RELATED APPLICATIONS

This application claims the benefit of PPA Ser. No. 61/386,507 filed 2010 Sep. 25 by the present inventor, which is incorporated herein in its entirety by reference.

FEDERALLY SPONSORED RESEARCH

Not Applicable

SEQUENCE LISTING OR PROGRAM

Not Applicable

BACKGROUND OF THE INVENTION

1. Field of Invention

This invention relates to the area of human vision correction, specifically relating to the use of short pulse laser beams to precisely remove ocular tissue to change the refractive power of the human eye.

2. Background of the Invention

The invention relates to procedures and apparatus for performing refractive surgery in the central aspect of the cornea to correct refractive errors of the eye. The invention uses ultrashort pulsed laser to perform all aspects of the corneal surgery, including the creation of incisions and the direct ablation of corneal tissue. In particular, the invention replaces the use of UV ablating lasers in procedures such as laser-assisted in-situ keratomileusis (LASIK) with an ultrashort pulsed laser.

Corneal Refractive Laser Surgery

Modern corneal refractive surgery techniques draw upon the original work of Dr. Jose I. Barraquer. Briefly, in 1958, Dr. Barraquer first developed keratomileusis techniques based on the removal of a lenticular volume of corneal tissue by mechanical means. In 1990, Pallikaris et al reported the use of an excimer laser was used to ablate the lenticular volume in the first LASIK cases. The development of LASIK and related procedures is described in Section Three, pages 147-222 of the text book "Refractive Surgery", 2nd edition, 2007, edited by Dimitri Azar.

In the development of corneal refractive correction with lasers, direct ablation of the corneal anterior surface with an ultraviolet (UV) laser was used. An early example is the method of L'Esperance, Jr. in U.S. Pat. No. 4,665,913. The UV laser was typically an excimer laser. The laser ablation was performed with repeated patterns of laser pulses arranged in a specific geometry. The pattern of ablating pulses produced a change in the corneal shape and therefore the refractive power of the eye. This procedure is called photorefractive keratectomy (PRK). The limits of this approach include the fact that direct ablation of the anterior layers of the cornea, including Bowman's layer and the anterior corneal stroma, produce tissue remodeling and a wound healing response that limit and degrade the optical outcome.

Laser-assisted in situ keratomileusis (LASIK) was developed to overcome the limits of PRK. In U.S. Pat. No. 4,840,175, Peyman first detailed the method which later came to be known as LASIK. In LASIK, a mechanical blade first makes a corneal flap cut. Subsequent manual lifting of the flap exposes the inner corneal tissue, referred to as the corneal stroma. The stroma is then subjected to an ablating UV laser beam. The ablating UV laser beam removes a volume of corneal tissue according to a specific mathematical prescription for producing the desired curvature change. In a later development, Munnerlyn in U.S. Pat. No. 5,163,934, employed a difference of sphere formulation to determine the lenticular volume to be removed for a treatment of myopia. The success of LASIK was swift, but used a two-stage, two-instrument procedure. A significant limitation of LASIK is the reliability, precision and quality of the blade cuts to produce the corneal flap. A second limitation is the requirement that nomograms be developed to compensate for the biological response to ablation, and to the geometry-dependent efficiency of UV laser ablation of the corneal stroma. A third limitation is that the low spatial frequency of the ablation patterns realizable with excimer laser ablation. That is, the lateral size of the ablation compared to the ablation depth of a single pulse makes it difficult to stack pulses in a way that allows for arbitrary ablation profiles. Typically, the profiles in LASIK and PRK vary slowly, which from a visual outcomes point of view is rather good. However, if a small amount of tissue is to be removed, such as may occur in a complication of refractive surgery, of if a higher order aberration is to be corrected by removal of a volume of tissue having relatively steeply angled features, large spot excimer ablation may not be efficacious.

LASIK and PRK are performed using a UV laser, typically an excimer laser, to perform the ablative part of the procedure. Examples of excimer laser keratomes include the Visx Star S4 from Abbott Medical Optics, Santa Ana, Calif.; the Technolas 217A from Technolas Perfect Vision GmbH, Munich, Germany; or the LADARVision 4000 and the Allegretto Wave from Alcon Laboratories, Inc., Fort Worth, Tex.

An alternative to LASIK and PRK was suggested and developed by Bille and Juhasz in U.S. Pat. No. 4,907,586 and further refined in U.S. Pat. No. 5,993,438. In this method, a focused ultrashort pulsed laser beam is scanned inside the cornea to create a defined volume of vaporized tissue consisting of many individual small-scale photodisruptions. The volume of tissue would be vaporized and ultimately resorbed by the surrounding corneal tissue. The resulting new corneal shape would produce the desired refractive correction. This approach is referred to as intrastromal or intrastromal ablation. A picosecond laser instrument by Intelligent Surgical Lasers was developed for this procedure. Limitations to the method were several. One limitation is the relatively large volumes of vapor produced in the stroma which limit the amount of tissue that can be destroyed or removed. A second limitation is that the vaporization of tissue for the purpose of altering the shape of the cornea through relaxation of the overlying anterior surface survace is limited by the natural stiffness of the corneal membranes. The native stiffness of the cornea limits the size of the refractive change that can be produced in this method.

Ultrashort pulsed lasers were commercially introduced into corneal refractive surgery with the development of femtosecond laser flap cutter instruments. Mourou et al in U.S. Pat. No. 5,656,186 described a method for using femtosecond pulses which allows for a more deterministic and precise machining of materials, including biological tissues, relative to picosecond lasers. Femtosecond lasers assist in the LASIK procedure by replacing the mechanical microkeratomes used in the corneal flap cutting step. The corneal cuts produced are precise and can have arbitrary three dimensional shapes, surpassing what can be achieved with mechanical blades. A limitation of the approach is that the actual refractive correction still requires the use of a second laser, namely an excimer laser.

Incisional ultrashort pulsed laser keratomes generate, process and deliver a train of scanned, tightly focused ultrashort laser pulses onto or into the volume of a fixed or immobilized cornea. The laser sources used generally employ a chirped pulse amplification technique with a large bandwidth lasing medium, such as Ti:S, Nd:glass or Yb:fiber. Typically, the laser pulses energies range from 0.1-10 microJoules, the pulse widths are <1 picosecond, the beam quality is near-diffraction-limited, and the wavelength falls between the NIR and the visible (typ 800-1100 nm) so as to avoid significant heating of water or tissue by linear absorption in the corneal tissue. Commercially available instruments operate at laser repetitions between 30 kHz and 2 MHz, depending on the design, model and manufacturer. A high speed 2D beam scanner in combination with a high numerical aperture focusing objective allows for the precise placement of tightly focused spots throughout the volume of the human cornea. In a typical femtosecond laser keratome the cornea is fixed with respect to the keratome optical axis and the cornea is lightly held in place and applanated by a contact glass and suction ring.

A purely incisional approach to refractive surgery using a single ultrashort pulsed laser instrument was taught by Juhasz in U.S. Pat. No. 6,110,166. In this approach, multiple laser cuts define a disk-shaped block of corneal stromal tissue underlying a laser-cut flap. The flap is manually lifted and the disk-shaped corneal plug or disk is manually removed. When the flap is replaced, the change in the corneal shape resulting from the missing corneal tissue lenticle produces an appropriate change in refractive power. This change can be accomplished without the need for an ablation step by a UV laser. The approach was similar to an earlier refractive surgery performed with a mechanical blade. The mechanical approach was called automated lamellar keratoplasty or ALK, introduced by Ruiz et al in U.S. Pat. No. 5,133,726. A limitation of both the ALK and the femtosecond laser keratomileusis procedure was the relatively poor refractive outcomes associated with removing a disk of planar geometry, rather than a disk of the ideal lenticule shape according to Munnerlyn and others.

An improved approach over Juhasz is found in United States Patent Application No. 20080319428 of Weichmann et al. The volume of the stromal disk of tissue to be laser cut and manually removed have anterior and posterior surfaces having curvatures rather than being planar. The invention advantageously allows for the realization of ideal shapes of the tissue to be removed. A limitation is that the tissue to be removed manual after cutting may tear or fragment, and cannot easily be removed by laser or by other means. A related limitation is that the axial thickness of the tissue to be removed may be associated with a minimum thickness. Some refractive corrections may require cutting a thin cross section volume of tissue. If the tissue is too thin, it may be too friable. This aspect places limitations on the ranges of potential refractive corrections achievable by this method. A further limitation is that the gas produced in the first portion of tissue vaporized may produce movement or changes in the cornea that interfere with the vaporization of subsequent portion of tissue.

U.S. Pat. No. 4,907,586 also contains a method of corneal refractive surgery in which the optical properties of the cornea are directly altered by a scanning ultrashort pulsed laser. In this method, index of refractive of the targeted volume produces the desired refractive correction. A limitation of this method is the size and stability of the refractive changes to the cornea.

Direct Ablation of Tissue

In LASIK, excimer lasers directly photoablate the corneal tissue they impinge upon. The controlled ablation of corneal stroma tissue produces the desired shape change.

Ultrashort pulsed lasers, such as femtosecond lasers, are widely used to incise cornea through the mechanism of photodisruption. Present clinical use of ultrashort pulsed lasers in the eye employs photodisruption and not the true ablation associated with excimer lasers in cornea. That is, ultrashort pulsed lasers are used to cut cornea rather than ablate it. This is quite sensible in that the natural advantage of using an ultrashort pulsed laser in transparent tissue is that highly localized, small photodisruption events can be arranged to create cut planes or surfaces.

Some confusion exists in the art about the term "ablation". When ultrashort pulsed lasers are used in ophthalmic surgery, the laser-tissue interaction is generally the creation of incisions through the cumulative effect of many individual photodisruption events. In physical processes, ablation refers to the physical processes, such as melting and vaporizing, that result in the ejection of material from the ablation site. The confusion is likely due to the use of the term ablation in medicine. In medical usage, ablation means the localized destruction of tissue, but not usually the physical ejection of tissue through melting or vaporization.

An aspect of my invention is physical ablation of corneal and ocular tissue with ultrashort pulsed lasers. I therefore differentiate between the usage of the term "ablation" in the prior art of ultrashort pulse lasers and the meaning of term is used in my invention. Here, when I use the term "ablation" with ultrashort pulsed lasers, I mean the physical removal of tissue resulting from the laser interaction, whether as a result of a photodisruption event or by some other interaction. Typically I use the term "ablative mode" in this context. When referring to the creation of cuts or incisions, I will use the term "incisional mode".

Two examples of this confusion in terminology are found in Zhang et al ("Morphologic and histopathologic changes in the rabbit cornea produced by femtosecond laser-assisted multilayer intrastromal ablation", IOVS, May 2009, Vol. 50, No. 5.) and Wang et al ("In-vivo intratissue ablation by nanojoule near-infrared femtosecond laser pulses", Cell Tissue Res 2007, Vol. 328:515-520) In the first reference, the authors use the term ablation, but the actual laser-tissue interaction in the cornea was intrastromal photodisruption, which was arranged to create multiple dissection planes inside the cornea. In the second reference, the authors also use the term ablation, but again the laser-tissue interaction was the photodisruptive destruction of corneal tissue on a small scale by nanoJoule laser pulses. True ablation was not occurring in either case.

Certainly ultrashort pulse laser ablation is used in a wide variety of material processing applications. However, the use of ultrashort pulse laser ablation of exposed cornea surfaces for clinical procedures is limited by several factors. An important limitation is the limits placed on input average power and input pulse energy to the cornea by safety considerations associated with non-target tissues such as the retina. A second limitation is the requirements placed on the positioning of a tightly focused laser spot at or near the target surface. This limitation in consideration of available practical ultrashort pulse laser sources results in micron precision in the positioning of the laser focus with respect to the target tissue surface. It is a further limitation that when positioning registration of a focused ultrashort laser beam with respect to a target tissue surface is achieved, very small motion associated with the involuntary movements of the eye may interrupt tissue ablation before a meaningful volume of tissue can be ablated.

Posterior Flap Ablation

The stromal surface targeted for laser ablation is created by manually lifting and reflecting the anterior flap of tissue produced by blade or ultrashort laser cutting. It is generally advantageous to target the exposed stromal bed for excimer laser ablation. In some excimer laser treatments, it may be advantageous to target the posterior surface of the lifted flap instead of the stromal bed. For example, Maldonado retreated LASIK patients by lifting a flap, manually marking the corneal flap anterior surface and manually directing an excimer ablation pattern with the laser keratome eye tracking system turned off ("Undersurface ablation of the flap for laser in situ keratomileusis retreatment", Ophthalmology Vol. 109, No. 8, August 2002). Maldonado marked the posterior flap surface with Gentian violent ink and a hand instrument referred to as a para-radial marker. He relied on visualizing the marked pattern and manually orienting the laser ablation pattern. He noted that a major challenge was stabilizing the eye and flap, and used hand instruments to stabilize the flap, relying on the reflected flap to lie on the eye anterior surface for the ablation. A limitation of the approach of Maldonado is the poor stability of the reflected flap tissue subject to laser radiation. A secondary limitation is the uncertainty in the positioning of the flap posterior surface. These limitations are less important in the case of excimer laser pulse interaction, but are important in the potential use of tightly focused ultrashort pulses, a feature of my invention.

Eye Tracking and Corneal Marking

The corneal is usually marked for refractive surgery. In LASIK or other laser refractive surgery, hand instruments inked with Gentian violet or another biocompatible dye are used to demarcate the corneal center, the optical zone or other orientation information to facilitate the positioning and placement of both the flap cutting keratome and the excimer laser keratome instruments. Marking is typically done by hand or with hand instruments. Marking is used to center and orient the placement of microkeratomes or the placement of excimer laser treatments. A typical hand instrument for marking the cornea in preparation for laser refractive surgery is taught by Kritzinger in U.S. Pat. No. 5,752,967. Further examples of marking instruments may be found in the extensive catalog of manual instruments available from Katena Products, Inc, Denville, N.J.

The biocompatible inks used for corneal marking can be oil-based or water-based inks. Water-based inks—typically a formulation of Gentian violet dye—do not bind strongly to the cornea. In fact, the water-based ink washes off quite easily, and tears, blinking or eye drops can easily fade the markings before the laser procedure. For this reason, oil-based inks are often preferred. According to Ide et al ("Effect of marking pens on femtosecond laser-assisted flap creation", J Cataract Refract Surg 2009; 35:1087-1090), a limitation of oil-based inks is the tendency for the inks to interfere with the transmission of ultrashort or femtosecond laser beams used to create corneal flaps. A further limitation of oil-based inks is the difficulty of removing the inks after the laser procedure is complete.

Laser surgery of the cornea requires precise placement of the laser pulses with respect to the location of the tissue surfaces. Voluntary and involuntary movement of the eye relative to the laser beam optical axis may prevent the desired placement of pulses. Saccadic and slower drifts of the eye may be mitigated by instructing patients to fix their gaze on a distant object or image. The human eye during directed fixation of the gaze exhibits three types of involuntary motion: tremor, microsaccades, and drifts (Physiology of the Eye, Dawson ed., page 663). These movements occur on several time and amplitude scales. Additionally, voluntary or reflexive motion may occur depending on the patient's mental state and environmental stimuli. In corneal refractive laser surgery a need exists to compensate for these movements. These approaches are useful, but insufficient for precision laser surgery of the cornea by excimer lasers, and less useful in ultrashort pulsed laser surgery of the cornea.

A mechanical means to restrain the subject eye may also be used. Restraining the eye generally requires pressure or low vacuum forces to be applied to some part of the anterior portion of the eye globe. The application of such forces can lead to discomfort, injury and surgical complications. Additionally, restraining the eye is not sufficient for all eye motion.

A well-established feature of LASIK and other laser-based corneal refractive surgeries is the detection of, and compensation for, eye movements through the use of eye-tracking technology. Typically, eye trackers employ multiple digital cameras to image high contrast anatomic structures, such as the iris or the pupil edge. Software and firmware processing of the images then produce image registration information that is used to track the motion of defined features. An early example of eye tracking for PRK was taught by Smith in U.S. Pat. No. 5,350,374. Eye tracking may be used passively or actively. Passive eye tracking halts laser treatment when the eye motion ranges beyond an acceptable limit. Active eye tracking continuously compensates for eye motion by re-directing the beam position and angle to match eye movement. A limitation of eye tracking technology with respect to potential use in ultrashort pulsed laser treatments is that the highest speed eye tracking technology available works in the kHz range, or has an equivalent bandwidth. Femtosecond lasers used to incise cornea now operate in the 100's of kHz range. The present invention optimally uses laser sources of pulse repetition rate above 1 MHz pulse repetition rate. A limitation of the existing eye tracking art is that the speed of eye trackers does not match the high repetition rates of ultrashort pulsed lasers that can perform clinically relevant ablation rates in an unrestrained cornea.

An alternative approach is the use of radar technology as in the Ladarvision 4000, Alcon, Inc.

In ultrashort pulse corneal surgery, eye tracking is not performed. The distance tolerances for positioning the focused laser beam and the scanning path of the focus with respect to the corneal surface are high, and are typically on the order of a few microns. The invention taught by Juhasz in U.S. Pat. No. 6,254,595 uses an applanating optic in combination with a "skirt" that uses suction to apply a ring of suction force to the eye. This approach, essentially universal with ultrashort pulsed laser keratomes for corneal surgery, functions well for the incisional modality used presently by all commercial instruments. Applanating optics may be planar, as in the invention of Juhasz, or they may have a curved surface conforming to the shape of the cornea. These solutions work well for ultrashort pulsed laser incision cutting, because there is no need to allow material to be ejected from the target surfaces. A limitation of applanating devices is that direct ablation cannot be done at the same time. A means of placing tightly focused ultrashort pulsed laser pulses at targeted surface(s), with the targeted surface(s) unobstructed, is needed to enable the ablation modality of the present invention.

Bille et al teach the use of laser-produced bubbles on the surface of the cornea to serve as tracking features for a laser-based tracking system in U.S. Pat. No. 4,848,340. One limitation of this invention is the low contrast that a surface ablation feature on the cornea presents. A second limitation is the undesirability of introducing additional injuries or lesions to the surface of the cornea.

In U.S. Pat. No. 6,579,282, Bille et al teach the placement of bubbles created inside the corneal stroma by laser photoablation, with the bubbles serving as guide features for image-based eye tracking systems. The bubble features for eye tracking are created rapidly by a scanning laser, and may be created by an ultrashort pulsed laser. A limitation of this approach is the low contrast bubbles may present to eye tracking systems. A second limitation is that laser-generated bubbles in stroma dissolve and are resorbed in the corneal tissue over time. A third limitation is the well-known phenomenon from ultrashort pulsed laser corneal surgery in which bubbles created by laser vaporization in the corneal stroma move along lamellar planes in unpredictable ways.

3. Objects and Advantages

Accordingly, in addition to the objects and advantages of the apparatus and methods described in my above patent, several objects and advantages of the present invention are:
 a) to provide a means of inducing a refractive change in the human eye by direct removal of corneal tissue with ultrashort pulsed laser ablation;
 b) to provide a means for ablating stromal tissue on the posterior surface of an exposed corneal flap with an ultrashort pulsed laser;
 c) to provide a means of allowing the use of high average power and high pulse energy ultrashort pulsed laser beams to ablate ocular tissue that exceed safe limits when used on an exposed corneal stromal bed as in LASIK or related treatments;
 d) to provide a means of producing ablation profiles of ocular tissue of high spatial modulation;
 e) to provide a means of ablating and thereby removing tissue with small lateral dimensions as in an adhesion or tag of corneal tissue;
 f) to provide a means of removing sections of corneal tissue of thickness smaller or more friable than can be safely removed and cut by incisional means;
 g) to provide a means of ablating ocular tissue with high pulse rate ultrashort pulsed lasers that allows for relaxed positional tolerances between target tissue and ablating beam;
 h) to provide a means of ablating ocular tissue with high pulse rate ultrashort pulsed lasers using an imaging eye tracking system to compensate for involuntary motion of the eye;
 i) to provide a means of incising or ablating ocular tissue with ultrashort pulsed lasers without the need for an applanating optic in contact with the cornea;
 j) to provide a means of creating high contrast fiduciary marks in cornea for use with an image-based eye tracking system;
 k) to provide a means of creating fiduciary mark features in human cornea with ultrashort pulsed laser incisions having sufficiently small width so as to avoid interfering with visual acuity of the patient;
 l) to provide a means of creating fiduciary mark features in human cornea with ultrashort pulsed laser incisions which can be selectively impregnated with water-based dyes;

One advantage of the present invention is that a single laser platform may be used to perform corneal refractive surgery, eliminating the need for two separate and expensive laser systems. A further advantage is that the invention may be used to create incisions and to directly ablate tissue to create a refractive effect, allowing a single instrument to perform many of the procedures presently performed by various laser and non-laser keratome instruments. A further advantage is that the invention requires less direct contact with the eye relative to other ultrashort laser keratomes, offering the possibility of vision correction procedures that are less invasive than at present. In particular, some incisional procedures may be performed without the need for an applanating optic in contact with the cornea. Such minimal touch surgical procedures reduce the risk of infection, allow for greater patient comfort, and are associated with lower complication rates.

Further objects and advantages will become apparent from a consideration of the drawings and ensuing description.

SUMMARY

In accordance with the present invention a refractive laser apparatus comprises an ultrashort pulsed laser engine that produces a focused scanning laser beam directed onto the human eye. The laser beam is guided by optical tracking subsystems. The present invention operates in both an incisional mode to cut tissue and in an ablative mode to remove tissue for purpose of correcting refractive errors in the human eye.

DRAWINGS—LIST OF FIGURES

In the drawings, closely related figures have the same figure number, but have different alphabetic suffixes.

Figure 2A:
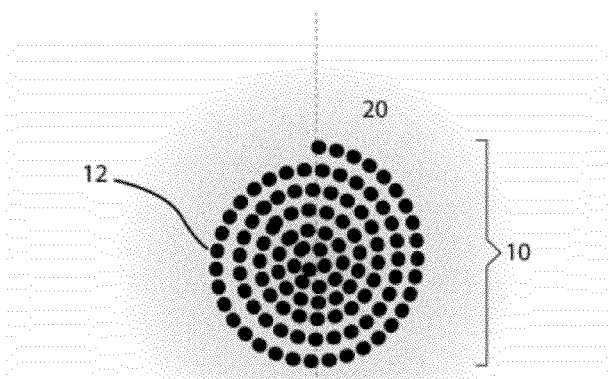
Figure 2B:
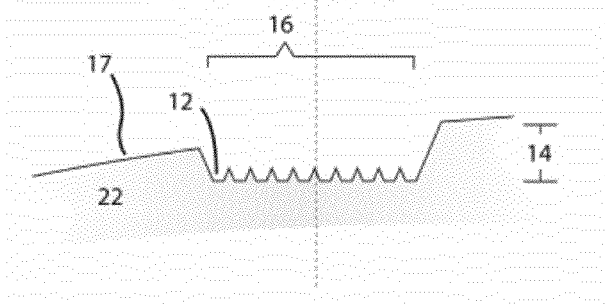
Figure 2C:
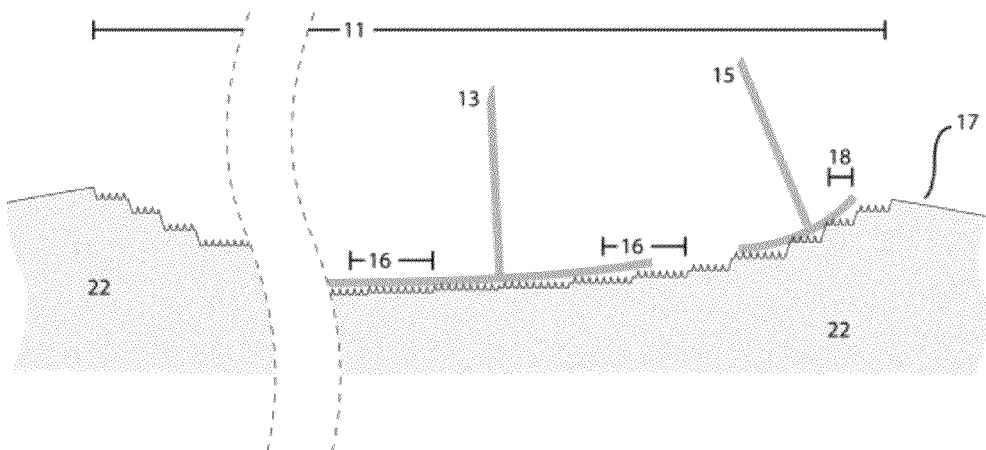
Figure 3A:
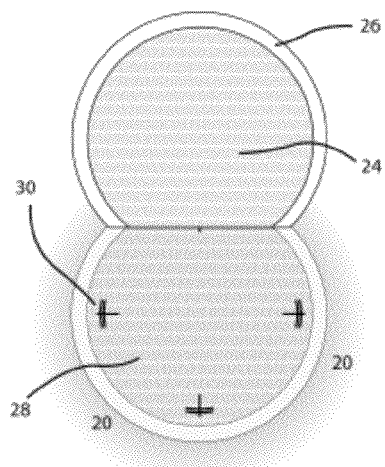
Figure 3A:
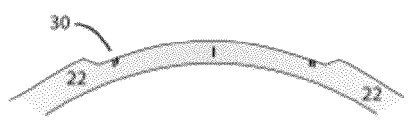
Figure 3B:
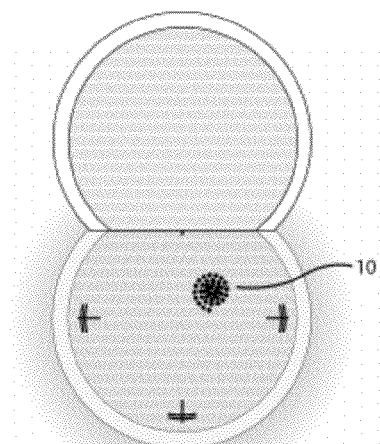
Figure 3B:
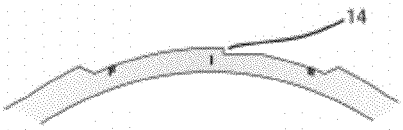
Figure 3C:
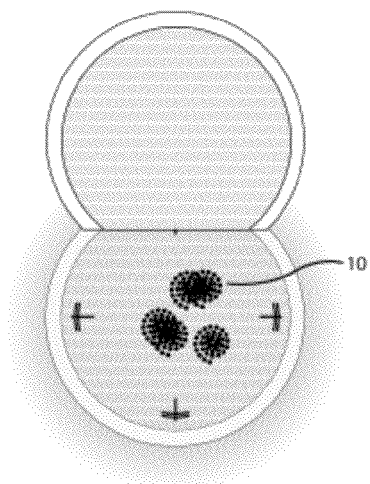
Figure 3C:
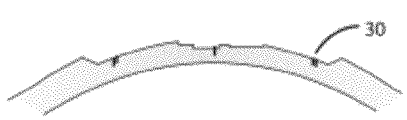
Figure 3D:
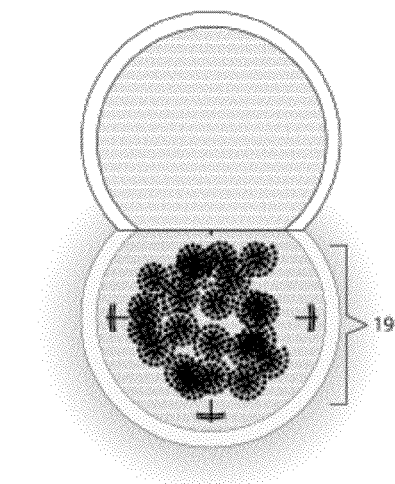
Figure 3D:
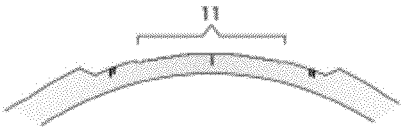
Figure 4A:
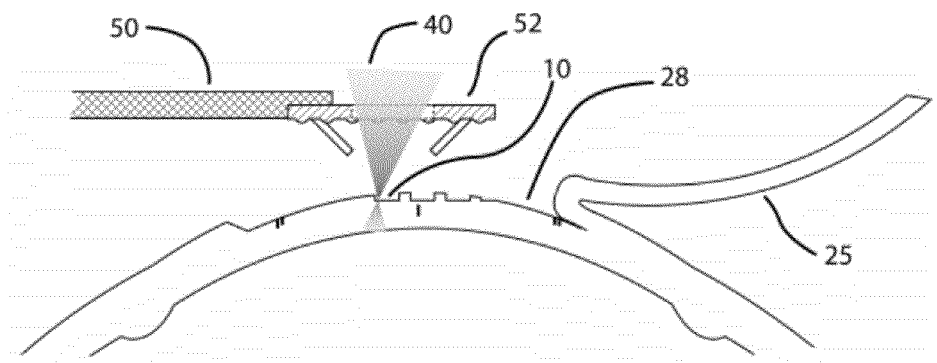
Figure 4B:
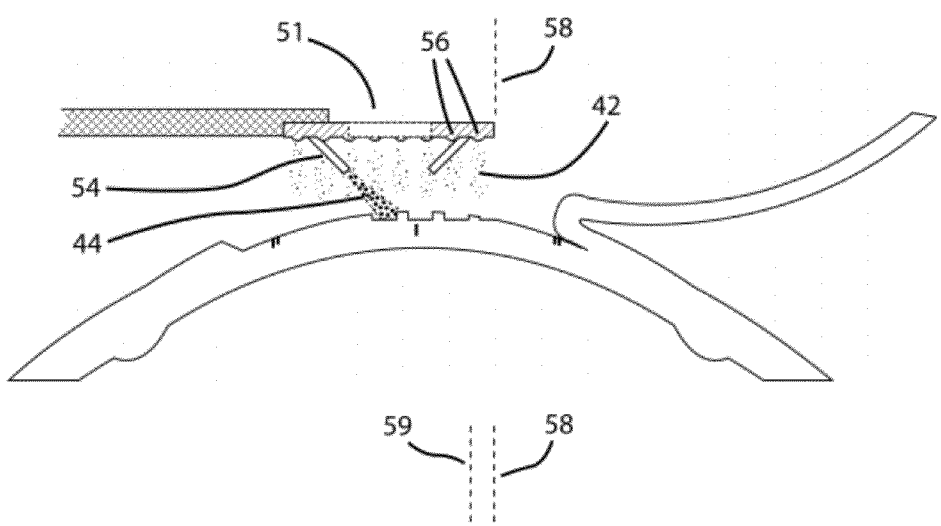
Figure 4C:
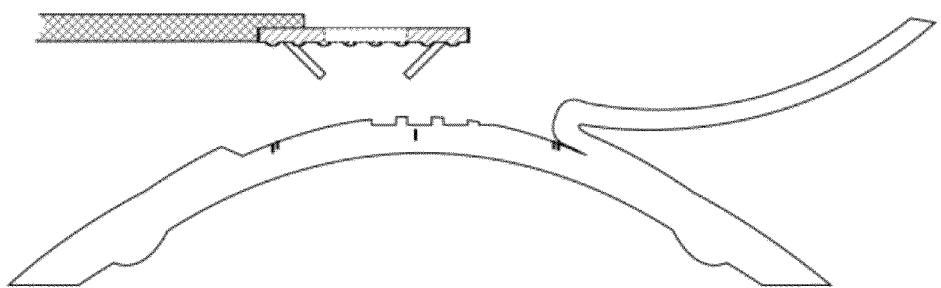
Figure 4D:
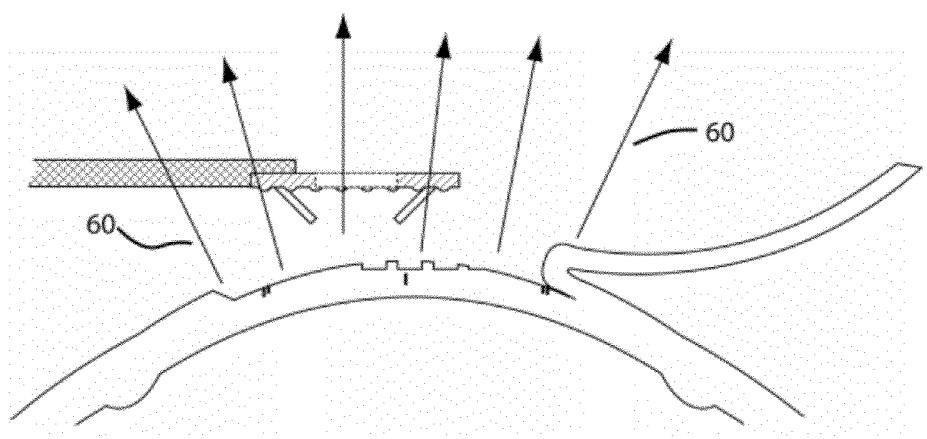
Figure 4E:
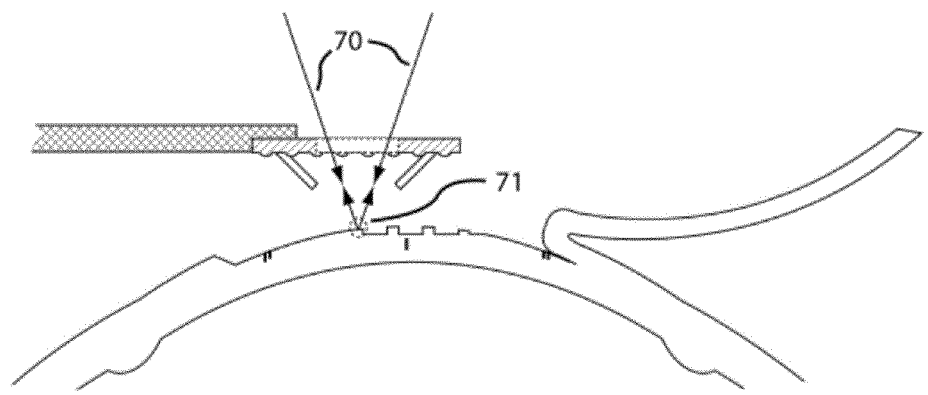
Figure 5A:
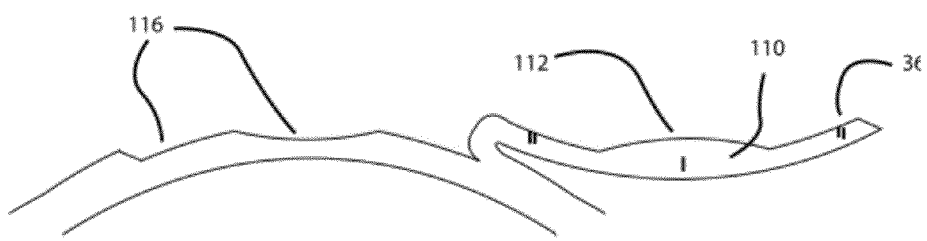
Figure 5B:
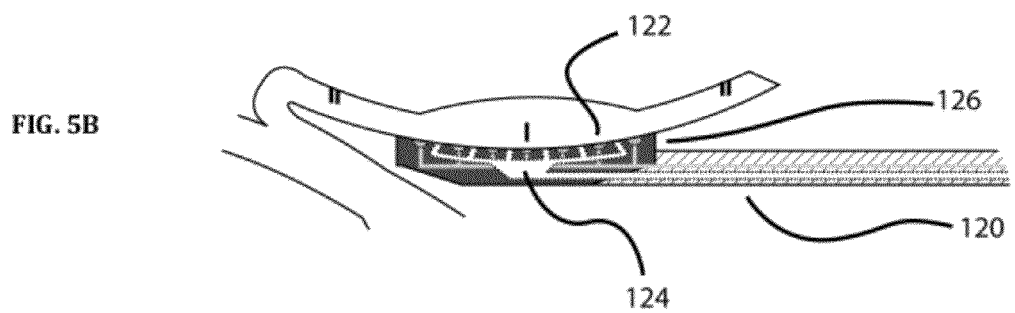
Figure 5C:
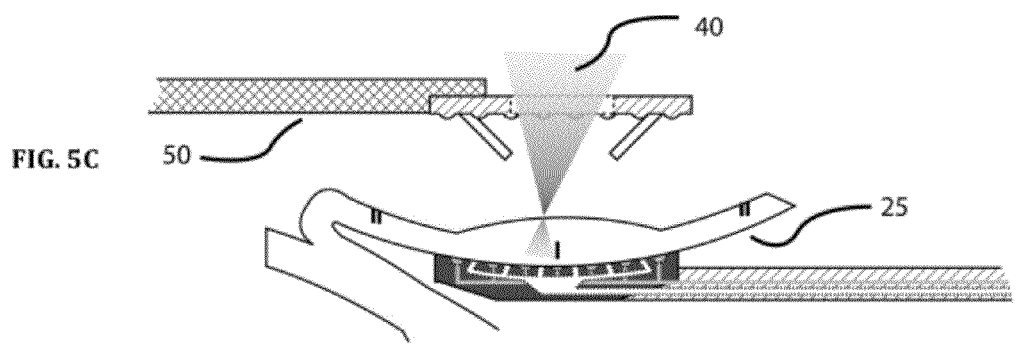
Figure 5D:
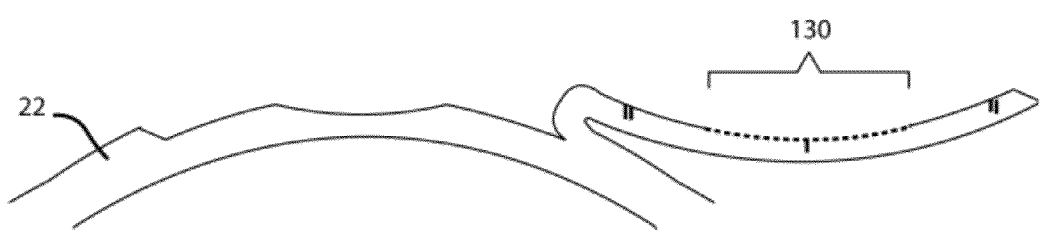
Figure 5E:
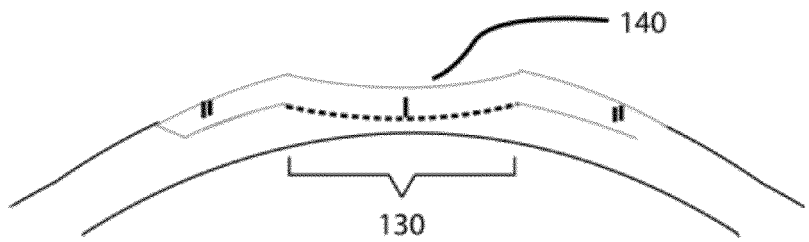
Figure 6:
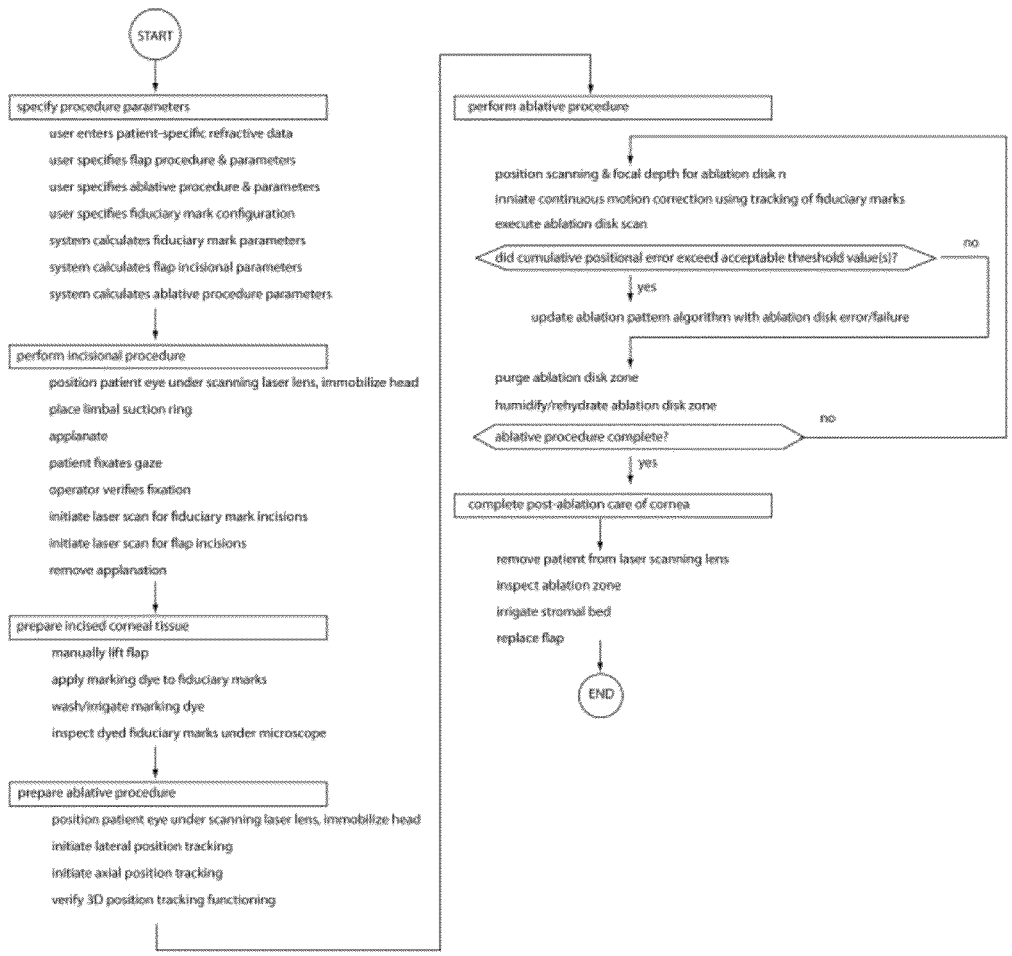
Figure 7:
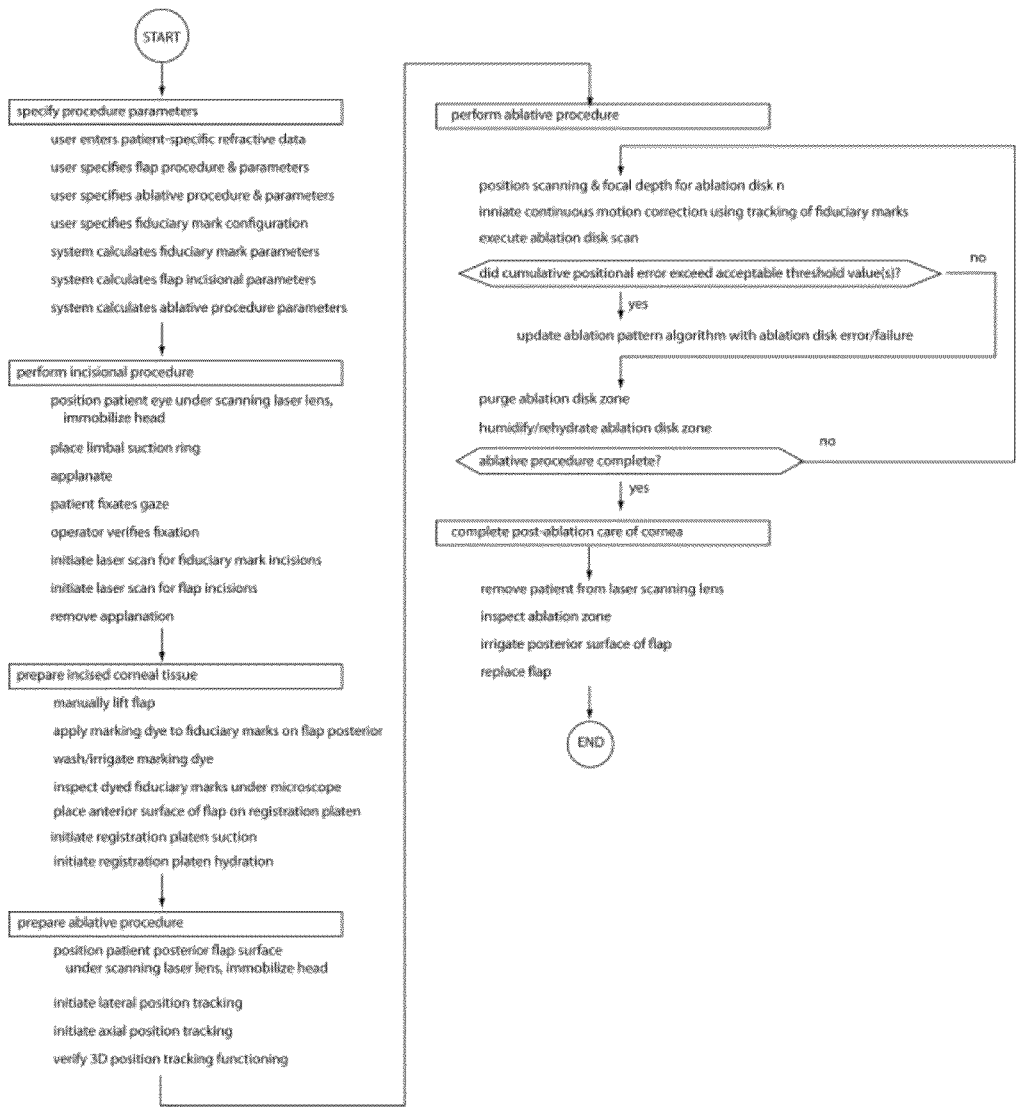

FIG. 1 is a representation of the invention performing a posterior flap surface ablation surgical procedure FIG. 2A is a top view of a representation of a single ablation disk in corneal tissue FIG. 2B is a side view of a representation of a single ablation disk FIG. 2C is a side view of completed representative ablation profile in cornea FIG. 3A shows both side and top view of exposed corneal stromal bed with laser-cut fiduciary marks FIG. 3B shows both side and top view of corneal stromal bed with single ablation disk completed FIG. 3C shows both side and top view of stromal bed with multiple ablation disks completed FIG. 3D shows both side and top view of stromal bed with completed ablation profile FIG. 4A depicts side view of laser ablation process operating on exposed stromal bed FIG. 4B depicts side view of post-ablation processes operating on exposed stromal bed FIG. 4C depicts side view of repositioning of ablation assist arm after ablation sequence FIG. 4D depicts side view of image acquisition step of surgical field for use in optical tracking FIG. 4E depicts side view of confocal optical signal acquisition for sensing z-position FIG. 5A is a side view of creation of non-planar corneal flap for posterior surface ablation FIG. 5B is a side view of non-planar corneal flap fixed on registration platen for posterior surface ablation FIG. 5C is a side view of posterior flap surface ablation process FIG. 5D is a side view of completed posterior flap surface ablation process FIG. 5E is a side view of curvature change in cornea following posterior flap surface ablation FIG. 6 illustrates a preferred process flow for refractive procedure using direct stromal bed ablation FIG. 7 illustrates a preferred process flow for refractive procedure using posterior flap ablation FIG. 8A shows side view of incision and fiduciary mark cutting with anterior chamber anatomy FIG. 8B shows expanded side view of laser incision and fiduciary mark cutting FIG. 8C shows side view of application of fiduciary mark contrast agent FIG. 8D shows top view of completed stromal fiduciary marks with impregnated contrast agent

DRAWINGS—GUIDE TO THE FIGURES

FIG. 1 is a representation of the complete invention in the process of performing a refractive procedure in a preferred embodiment. Laser source 200 is processed in optical processing module 210, passes scanning beam delivery module 220, and is coupled into focusing optics module 230. Focusing optics module 230 focuses and impinges laser beam 40 upon non-planar posterior flap surface 112 affixed to registration platen 120. Registration platen actuator module 262 actuates and positions registration platen 120. Registration platen 120 contains hydration manifold 126. Ablation assist arm 50 contains an aperture that transmits focused laser beam 40. Ablation assist arm 50 actuates and positions assist arm actuator module 260. Digital cameras 250 image illumination rays 60 and relay images to processor 270. Axial position sensing module 240 collects confocal signal from focusing optics module 230 and relays signal to processor 270.

In FIG. 2A a single ablative disk 10 in tissue is shown. Ablative disk 10 is shown as a disk consisting of a series of individual laser ablation sites 12 arranged in a spiral produced by a scanning laser focal spot. FIG. 2A shows the view from above the tissue, which is preferentially corneal stroma, though other tissues may be ablated in other applications of the invention. FIG. 2B indicates ablation disk 10 in schematic side view of corneal stroma 22, though other ocular tissues may be targeted. Characteristic depth 14 of ablation disk 10 may result in a graded depth profile relative to the curvature of the exposed corneal or stromal tissue surface 17. Ablation disk 10 has characteristic diameter 16, though for other shapes more than a single value may characterize the lateral extent of the ablation feature. Other ablative feature geometries are possible, including a raster scan of polygonal geometry, annular rings, elliptical disks, and other planar shapes. The smoothness of the ablation disk is characterized by a surface roughness value that depends on the separation of individual laser ablation shots 12, the separation of the shots and the values of the laser parameters used.

FIG. 2C depicts a completed ablation profile 11 located centrally in unablated tissue surface 17. Ablation profile 11 is created by placement of a series of ablation disks of diameter 16 with appropriate positioning, overlap and depth. Design of ablation profile 11 can result in a complex shape with distinct radius of curvature 13 and radius of curvature 15 characterizing the profile, and thereby the new refractive power of the cornea. The minimum radius of curvature achievable in ablation profile 11 is determined by the minimum horizontal overlap 18 of ablation disk features and characteristic depth 14 associated with a single planar ablation disk 10. Ablation profile 11 may also be constructed with a highly localize geometry, for example, as may be optimal for the removal of a small tissue adhesion or non-uniformity in the cornea. Ablation profile 11 may also be constructed with high spatial modulation amplitudes to generate corrections for high order aberrations.

FIG. 3 is a sequence in the tissue ablation process, with the tissue depicted being human cornea. Both side and top views are shown.

FIG. 3A shows an exposed stromal bed 28 of a human cornea just prior to beginning the ablation process. A top view of unaltered cornea 20 is shown at the top of the figure, while a side view of cornea cross section 22 is shown at the bottom of the figure. An already-cut corneal flap has been lifted and reflected to expose the posterior surface 24 of the flap and the edge or side cut 26 of the flap. Fiduciary marks 30 are used to locate the ablation with respect to the correct optical axis (fiduciary mark fabrication is shown in FIG. 8A-D).

FIG. 3B depicts the side and top view of the exposed corneal stromal bed of FIG. 3A, with a single ablation disk 10 created at a first location specified by a computed ablation profile sequence of individual ablation disks. Characteristic depth 14 of ablation of ablation disk 10 is indicated as a step in the stromal bed curvature at the bottom of FIG. 3B.

FIG. 3C depicts side and top views of the exposed corneal stromal bed of FIG. 3A after a number of ablation disks have been created at positions pre-determined by the requirements of the desired ablation profile.

FIG. 3D depicts side and top view of the exposed corneal stromal bed of FIG. 3A after completion of ablation profile 11, which consists of complete collection 19 of individual ablation disks 10.

FIG. 4 is a series of figures illustrating the ablation of corneal tissue as in FIG. 3, with the ancilliary processes that control and assist in the ablation process also shown.

FIG. 4A depicts a side view of cornea 22 with a flap already cut, lifted and reflected with corneal flap anterior surface 25 facing away from the focused laser beam 40. Exposed stromal bed 28 already has a sequence of ablation disk features created, with creation of single ablation disk 10 in process. Single ablation disk 10 is one in a sequence of scanned ablation disks. Ablation assist arm 50 is mounted on a motion control system integrated in the laser console (not shown). Aperture plate 52 contains central aperture 51 that allows focused laser beam 40 to reach corneal stromal bed 28.

FIG. 4B shows a side view of ablation assist arm 50 performing ablation assist processes. Nozzle 52 directs purge fluid 44 onto the local ablation area associated with ablation disk 10. Purge fluid 44 may consist of pressurized air, water, saline, or other fluids or fluids mixture compatible with biological tissue and useful for removing by pressure and direct contact any ablation products. At the same time, or alternatively, at a different time sequence, moisture or mist 42 may be supplied to the corneal tissue by hydration ports 56.

FIG. 4C shows a side view of the repositioning of ablation assist arm 50 from position 58 to subsequent position 59. The repositioning of ablation assist arm 50 occurs in order to ready ablation assist arm 50 for the next ablation disk in the planned sequence. The repositioning occurs under motion control elements which center aperture 51 and other associated ablation assist features of ablation assist arm 50 over the next target tissue location.

FIG. 4D shows a side view of a representative image acquisition step. Scattered illumination rays 60 originating from the surgical field are used by an image processing subsystem in the laser console (not shown in FIG. 4D) to analyze the relative lateral position of the laser optical axis with respect to the cornea.

FIG. 4E shows a side view of the acquisition of a confocal optical signal which locates the z-position or depth position of the focused laser beam relative to the target tissue surface. Confocal volume 71 produces optical radiation that is collected as confocal image beam 70 and relayed to detectors in axial position sensing module 240 (not depicted in FIG. 4E).

FIG. 5 contains a series of graphics illustrating an embodiment in which the posterior surface of a non-planar corneal flap is ablated to produce the desired refractive change in the cornea.

FIG. 5A depicts a side view of a cornea that has had a non-planar flap cut by ultrashort pulsed laser incision. The flap cut contains non-planar posterior flap surface 112 and planar posterior flap surface 110. The non-planar flap cut may be performed with or without the use of the well-known applanating optics described in the art of femtosecond laser keratomes. The peripherally located planar posterior flap surface 110 is parallel to the corneal anterior surface, but non-planar posterior flap surface 112 has a curvature that is not parallel to the corneal surface. Fiduciary marks 36 are produced as in FIG. 8, but with the incisions being made in planar posterior flap surface 110 rather than in the stromal bed 116.

FIG. 5B shows a side view of the corneal flap of FIG. 5A now affixed to registration platen 120. Registration platen 120 is connected to a micropositioning subsystem in the laser system (not shown) and can be used to move or position the flap in three translational dimensions with micron-level precision. Registration platen 120 is connected to a micropositioning subsystem in the laser system (not shown) and can be used to move or position the flap in three translational dimensions with micron-level precision. Registration platen 120 may also in some embodiments have the ability to gimbal or rotate the center of the corneal flap with respect to one or more rotational axes to orient the posterior flap surface with respect to the ablating femtosecond beam 40. Registration platen interface 122 of registration platen 120 may be a disposable element. Registration platen interface 122 has a smooth curved surface designed to match a typical human corneal surface. To aid in the mechanical fixation of the corneal flap on registration platen interface 122, manifold 124 of low vacuum level may be integrated into element 122. Manifold 124 may be supplied with low suction force or vacuum from vacuum lines in registration platen 120 connected to the laser system (not shown). Additionally, hydrating features 126 may wick, bleed or flow small amounts of physiologically appropriate fluid such as buffered saline to the flap anterior surface. Hydrating features 126 may be connected to a supply of fluid through a pump or reservoir of fluid in the console (not shown).

FIG. 5C illustrates a side view of the laser ablation step in posterior flap ablation. Laser beam 40 is focused and scanned over non-planar posterior flap surface 112. An ablation profile is built up as illustrated in FIG. 2 and FIG. 3. Registration platen 120 may be used in conjunction with ablation assist arm 50 and ablation assist processes illustrated in FIG. 4.

FIG. 5D shows a side view of ablated posterior flap surface 130 of the posterior flap surface. Non-planar posterior flap surface 112 is designed and cut such that ablated posterior flap surface 130 results in a final posterior flap surface that is continuously parallel to the anterior corneal surface.

FIG. 5E shows a side view of the corneal flap after repositioning the flap onto exposed stromal bed 116. The result of the ablation of non-planar posterior flap surface 112 to yield ablated posterior flap surface 130 is a corneal flap of uniform thickness, similar to the flap geometry obtained in conventional microkeratome-generated corneal flaps. Ablated posterior flap surface 130 results in the corneal surface relaxing to a new position, giving rise to a new corneal shape 140 and refractive power. Functionally, this is equivalent to creating a flap, and incising and removing a lenticule of the same shape. It is also equivalent to the stromal bed ablation process outlined in FIG. 8, but is produced with exposing the interior anatomy of the eye directly to the ultrashort pulsed laser beam used for the ablation process.

FIG. 6 is a flow chart representing an embodiment of the invention, in which the process of producing a refractive correction in the human eye is performed by initially exposing a stromal bed surface through the cutting and lifting of a planar corneal flap, and subsequently directly ablating the stromal bed surface through successive sequences of scanned ultrashort pulsed laser patterns.

FIG. 7 is a flow chart representing an embodiment of the invention, in which the process of producing a refractive correction in the human eye is performed by initially affixing the anterior surface of a corneal flap upon a registration platen thereby exposing the non-planar posterior surface of the flap, and subsequently by directly ablating the posterior surface of the corneal flap through successive sequences of scanned ultrashort pulsed laser patterns.

FIG. 8 illustrates the creation of femtosecond laser cut fiduciary marks 32 used to optically track the lateral position of the cornea with respect to a subsequent femtosecond laser ablation process step. All sequences of FIG. 8 are shown with the anterior chamber of the eye and cornea shown in cross section.

FIG. 8A shows a side view of cornea 22, the orientation of the anterior segment anatomy with respect to the focused laser beam 40, and the incisional paths associated with a flap cut and the creation of fiduciary marks 32. Phakic lens 98 is attached to ciliary processes 96 by zonule fibers 93. Iris structure 91 anterior to the lens 98 creates pupil 97 at the posterior of humor-filled anterior chamber 95. Above these structures, cornea 22 is connected to sclera 94 by the limbus 92. The beam 40 is shown scanning across planned flap incision plane 82, having partially created flap incision 80. A separate scanning sequence has produced side cut 84 to allow access to the flap with surgical hand instruments.

In FIG. 8B, an expanded side view from FIG. 8A is shown. The focal position of the moving focused laser beam 40 results in individual and rapid photodisruption events 46. Photodisruptions 46 are created by the optical breakdown that the femtosecond laser beam intensity produces. Secondary processes from the optical breakdown such as acoustic shock wave generation and propagation, cavitation bubble formation and oscillation and eventual localized tissue vaporization produce the micro-surgical effect of photodisruption in the same manner as is known in the art associated with incisional femtosecond laser keratomes. Side cut 84 is shown as a hashed line, as are already-cut flap incision 80 and vertical fiduciary mark features 32. Planned flap incision 82 is shown as a dashed line. Incision 80, side cut 84, and fiduciary cuts 32 may be cut using the invention in combination with the well-known applanation optics described in the prior art of femtosecond laser keratomes. Alternatively, incision 80, side cut 84, and fiduciary cuts 32 may be cut without an applanating optic using an eye motion compensation system based on a lateral eye-tracking and z-position confocal sensor.

FIG. 8C shows an expanded side view of FIG. 8B after the flap (not shown) has been lifted from side cut 26 and exposing the interior of cornea 22. Application of a contrast agent 102 is made on the exposed cornea interior using applicator 100. Fiduciary marks 30 have been dyed, marked or stained with the contrast agent 102. Excess contrast agent 101 may be removed with irrigation or application of an absorbent wipe.

In FIG. 8D a top view is shown of the cornea in which the fiduciary mark dyeing or staining process steps have been completed and fiduciary marks 30 are visible with high optical contrast against the stromal bed 28.

DRAWINGS—REFERENCE NUMERALS 10 ablation disk pattern
11 completed laser ablation profile
12 single laser pulse ablation feature
13 a first characteristic radius of curvature of laser ablation profile
14 ablation disk pattern characteristic depth
15 a second characteristic radius of curvature of laser ablation profile
16 ablation disk characteristic diameter
17 unablated/uncut corneal surface
18 minimum overlap of adjacent disks
19 collection of individual ablation disk features
20 top view of corneal surface
21 anterior chamber anatomy
22 side view of cornea cross section
24 flap posterior surface
25 flap anterior surface
26 flap side cut
27 flap hinge
28 exposed corneal stromal bed
30 completed stromal fiduciary mark cut with contrast agent
32 completed stromal fiduciary mark cut
34 planned stromal fiduciary mark cut
36 contrast agent dyed posterior flap fiduciary mark
40 laser beam focal point
42 hydrating mist
44 purge gas or fluid
46 photodisruption event at laser focus
50 ablation assist arm
52 aperture plate
54 debris purge nozzle
56 hydration port
58 assist arm location for a specific ablation disk in sequence
59 repositioned assist arm location for next ablation disk in sequence
60 large field image acquisition rays
70 confocal rays to z-sensor
71 confocal volume
80 partially cut flap incision
82 uncut flap incision path
84 incision defining flap side cut
91 iris anatomy of human eye
92 limbus anatomy of human eye
93 zonule fibers anatomy of human eye
94 sclera anatomy of human eye
95 anterior chamber anatomy of human eye
96 ciliary processes anatomy of human eye
97 pupil anatomy of human eye
100 contrast agent applicator
101 excess contrast agent layer
102 contrast agent
110 planar posterior flap surface
112 non-planar posterior flap surface
116 exposed stromal bed
120 registration platen
122 registration platen interface
124 suction feature
126 hydration manifold
130 ablated posterior flap surface
140 replaced flap with ablated posterior surface
200 laser source
210 optical processing module
220 scanning beam delivery system
230 focusing optics module
240 axial position sensing module
250 digital cameras
260 assist arm actuator module
262 registration platen actuator module
270 processor

DETAILED DESCRIPTION a) Overview of Invention

The present invention is an ultrashort pulsed laser keratome. Laser keratomes are well known instruments for use in ophthalmic surgery. Ultrashort pulsed laser keratomes are generally used to create incisions in the cornea. A typical use of an ultrashort pulsed laser kerartome is the creation of corneal flaps in preparation for the vision correcting surgical procedures known as laser assisted in-situ keratomileusis (LASIK).

The present invention performs incisions in a similar manner as femtosecond laser keratomes, known in the art. Incisions in ocular tissues are produced by ultrashort pulsed laser keratomes through the creation of continuously connected patterns of individual photodisruptions. Photodisruptions result from the phenomenon of optical breakdown, which results when the intensity at the focus of a laser beam exceeds the ionization breakdown threshold of the target material. Ultrashort pulsed laser keratomes produce patterns of photodisruptions to create incisional surfaces, mimicking the action of a mechanical blade.

The present invention similarly scans patterns of tightly focused laser pulses inside the volume of transparent ocular tissue, or in a preferred embodiment, on the exposed surface of an ocular tissue such as cornea. The invention may be used to create incisions in this manner. The invention also performs direct refractive corrections through an ablative mode, not known in the art.

FIG. 1 depicts a preferred embodiment of the invention. Referring to FIG. 1, I now point out several major elements of the present invention. Laser source 200 generates a high repetition rate beam of laser pulses. Preferably, the pulses have pulse energies of 1-20 microJoules. The pulses are optimally less than 1 picosecond in duration. Optimal pulse repetition rates are at least 1 MHz.

The laser beam generated in laser source 200 is processed in optical processing module 210. Optical processing module 210 provides beam conditioning, beam shaping, beam energy monitoring, and other optical processing of the picosecond or femtosecond pulse train. The conditioning of the beam in optical processing module 210 results in a beam of characteristics suitable for launch into scanning beam delivery system 220. Techniques for shaping and monitoring ultrashort pulsed laser beams are well-known to those skilled in the art of picosecond and femtosecond lasers.

Referring again to FIG. 1, the ultrashort pulsed laser beam is routed into scanning beam delivery module 220. Scanning beam delivery module 220 contains high speed rotary scanners, such as galvanometric motors. The scanners in module 220 and the associated optics output a beam of continuously varying angle. The angular variation is designed to match the requirements of focusing optics module 230. Focusing optics module 230 produces focused laser beam 40 which impinges on the target ocular tissue. In a preferred embodiment, the target tissue is affixed to registration platen 120. Focusing optics module 230 also converts the angular variation in the input beam into a precision translation of the focus. High speed and continuous variation of the beam launch angle exiting focusing optics module 230 produces a continuously moving path of the focus of laser beam 40. The moving path of focused laser beam 40 may be designed to produce continuous patterns of individual laser pulses. Such an arrangement is known to those skilled in the art as an f-theta lens arrangement. Other approaches to produce a similar scanning focus are known in the art.

Patterns of scanned laser pulses are produced in target ocular tissue by scanning beam delivery system 210 in combination with focusing optics module 230. The patterns written by scanning beam delivery system 210 are advantageously designed to create a particular two-dimensional or three-dimension shape in the tissue. Incisional surfaces consist of many thousands or millions of micron-scale photodisruption events.

In a preferred embodiment, registration platen 120 affixes and maintains corneal flap surface at a controlled position. In FIG. 1, a corneal flap has been cut and lifted from anterior chamber of the eye anatomy 21 in a previous step of the surgical process. Non-planar posterior flap surface 112 is oriented to the focused laser beam 40 by registration platen 120. Registration platen 120 has a precision curved surface designed to conform to the anterior corneal surface, facilitating the orientation of non-planar posterior flap surface 112. Registration platen 120 also contains hydration manifold 126. Hydration manifold 126 applies hydrating fluid to the anterior corneal surface. Hydration manifold 126 also applies a low suction force to the anterior surface of the corneal flap, with the terms "anterior" and "posterior" corresponding to standard medical nomenclature.

The suction force and hydration fluid are supplied by registration platen actuator module 262. The suction force applied by hydration manifold 126 is sufficiently low to release flap in the event of movement.

Registration platen actuator module 262 also provides precision three-dimensional positioning control to registration platen 120. Processing control of registration platen actuator module 262 is performed by processor 270.

Ablation assist arm 50 assists in the ablation process. Ablation assist arm 50 is positioned proximate to exposed non-planar posterior flap surface 112. Ablation assist arm 50 contains an aperture that transmits focused laser beam 40. Ablation assist arm 50 provides purge fluid to assist the ablation of target tissue. Ablation assist arm 50 also provides hydration fluid to the target tissue. Ablation assist arm 50 is connected to assist arm actuator module 260. In a similar fashion to the functioning of registration platen actuator module 262, assist arm actuator module 260 supplies hydration fluid, purge fluid and precision motion control to ablation assist arm 50. Assist arm actuator module 260 positions ablation assist arm 50 in response to the commands from processor 270. The position of ablation assist arm 50 is determined by the particular location of an ablation sequence being executed. Ablation assist arm 50 is nominally centered over the target ablation site on an exposed tissue surface, for example, the exposed non-planar posterior flap surface 112 in FIG. 1.

In a preferred embodiment, the invention also includes an optical tracking system. Referring again to FIG. 1, one possible optical tracking system is shown. Digital cameras 250 capture images of the surgical field from illumination light rays 40 emanating from the surgical field and relay the captured images to processor 270. Image processing techniques, well known in the art, are used to construct difference information between consecutively acquired images. Relative lateral motion of the surgical field, for example, of non-planar posterior flap surface 112, is computed. Focused laser beam 40 may be adjusted to compensate for the detected motion. Alternatively, registration platen actuator module 262 may be commanded by processor 270 to reposition the corneal flap to compensate for the detected motion.

Other lateral optical tracking systems known in the art, such as laser-based systems, may be employed in other embodiments of the invention.

In a preferred embodiment, the invention also includes an axial position or depth optical sensing system. Axial position sensing module 240 in FIG. 1 detects the position of the tissue interface by the measurement of light intensity collected from the confocal volume of focusing optics module 230. The source of the confocal signal may be the laser itself, or may alternatively be supplied by coherent or incoherent illumination source in optical processing module 210. The size of the signal detected by axial position sensing module 240 is proportional to the distance between the tissue interface and the position of the focusing optics module 230. Dithering the focal position or the position of the tissue interface allows for a determination of the position of the interface to be made by software in processor 270. Alternatively, a computing processor may be located for this purpose in axial position sensing module 240. Alternatively, other optical-based approaches known in the art may also be used for the axial position sensing module.

b) Ablation Disks

Ablation of tissue in the present invention occurs through the photodisruption of tissue at or near an exposed or free surface upon which focused laser beam 40 impinges. The invention ablates ocular tissue by performing successive, stacked sequences of short duration ablation patterns. An individual ablation pattern or ablation sequence will be referred to as an ablation disk.

In the ablative mode of the present invention, the applanation and mechanical fixation features used in conventional femtosecond laser keratomes are not useful, applanation and mechanical fixation features may be advantageously used in alternative embodiments of the invention. Ocular tissues targeted for ablation preferably have an exposed and free surface.

In FIG. 2A a single representative ablative disk 10 in tissue is shown in top view. Ablative disk 10 is shown as a disk consisting of a series of individual laser ablation sites 12 arranged in a spiral produced by a scanning laser focal spot. FIG. 2A shows the view from above the tissue, which is preferentially corneal stroma, though other tissues may be ablated in other applications of the invention.

FIG. 2B indicates ablation disk 10 in schematic side view of corneal stroma 22. Characteristic depth 14 of ablation disk 10 may result in a graded depth profile relative to the curvature of the exposed corneal or stromal tissue surface 17. Ablation disk 10 has characteristic diameter 16, though for other shapes more than a single value may characterize the lateral extent of the ablation feature. Other ablative feature geometries are possible, including a raster scan of polygonal geometry, annular rings, elliptical disks, and other planar shapes. The smoothness of the ablation disk is characterized by a surface roughness value that depends on the separation of individual laser ablation shots 12, the separation of the shots and the values of the laser parameters used.

A number of patterns of individual ablation sequences may be used. Optimally, small diameter circular disks of spiraling lines of consecutive pulses are used. A preferred disk ablation pattern is shown in FIG. 2A. An individual ablation disk is optimally planar. Depth gradation of the overall ablation process is determined by the overlap and placement of disks of varying depth, that is, disks that are scanned at various positions along the optical axis or depth axis. During the actual laser ablation process, ablation sequences are overlaid in a way that the "islands" and edges of the ablation features overlap to result in a smoothly increasingly deep ablation profile.

An individual ablation disk diameter is determined by the repetition rate of the laser, the linear scanning speed and the amount of time allowed for an individual ablation sequence (itself determined by the time scale of the fixated eye motions), and by the desired spatial frequency and surface smoothness of the final ablation profile. FIG. 2B shows an ablation disk 10 of characteristic roughness <r>, where <r> is of the order of ablation disk characteristic depth 14.

c) Ablation Profiles

FIG. 2C depicts a completed ablation profile 11 located centrally in unablated tissue surface 17. Ablation profile 11 is created by placement of a series of ablation disks of diameter 16 with appropriate positioning, overlap and depth. Ablation disks 10 are arranged according to a predetermined ablation profile that depends on the desired refractive correction, following the prescriptions of Munnerlyn (U.S. Pat. No. 5,163,934) or other refractive correction algorithms known in the art. Geometric calculations are used to create the ablation prescription in advance of the procedure. The calculated ablation profile uses the input of the desired refractive change and initial corneal topography and shape diagnostic information supplied by clinicians prior to the procedure.

The design of ablation profile 11 can result in a complex shape with distinct radius of curvature 13 and radius of curvature 15 characterizing the profile, and thereby the new refractive power of the cornea. The minimum radius of curvature achievable in ablation profile 11 is determined by the minimum horizontal overlap 18 of ablation disk features and characteristic depth 14 associated with a single planar ablation disk 10. Ablation profile 11 may also be constructed with a highly localize geometry, for example, as may be optimal for the removal of a small tissue adhesion or non-uniformity in the cornea. Ablation profile 11 may also be constructed with high spatial frequency or spatial modulation to generate corrections for high order aberrations.

A minimal amount of time is allowed between each ablation disk 10 for the beam scanners to reposition for the production of the next ablation disk.

In this manner, creating ablation profile 11 is similar to the overlapping performed by large spot ablations performed in excimer or UV laser ablation of corneal tissue in LASIK. More generally, creating ablation profile 11 resembles the well-known process of overlapping laser pulses for machining a broad range of materials. In conventional laser processing of materials, the relatively shallow ablation depth of an individual laser pulse allows for overlapping and stacking of pulses to create a smooth, blended ablation profiles with some freedom to design the overall ablation profile, depending on the laser pulse character, and the ablation characteristics of single laser pulses in that material system. In the present invention, the sequence of laser pulses making up ablation disk 10 are similar to the individual, large area single pulses used in the conventional laser material processing example discussed above.

FIG. 3 illustrates the development of ablation profile 11 through the cumulative placement of collected ablation disk features 19. FIG. 3A shows an exposed stromal bed 28 of a human cornea just prior to beginning the ablation process. A top view of unaltered cornea 20 is shown at the top of the figure, while a side view of cornea cross section 22 is shown at the bottom of the figure. An already-cut corneal flap has been lifted and reflected to expose the posterior surface 24 of the flap and the edge or side cut 26 of the flap. FIG. 3B depicts the side and top view of the exposed corneal stromal bed of FIG. 3A, with a single ablation disk 10 created at a first location specified by a computed ablation profile sequence of individual ablation disks. Characteristic depth 14 of ablation of ablation disk 10 is indicated as a step in the stromal bed curvature at the bottom of FIG. 3B. FIG. 3C depicts side and top views of the exposed corneal stromal bed of FIG. 3A after a number of ablation disks have been created at positions pre-determined by the requirements of the desired ablation profile. FIG. 3D depicts side and top view of the exposed corneal stromal bed of FIG. 3A after completion of ablation profile 11, which consists of complete collection 19 of individual ablation disks 10.

Producing ablation of ocular tissue by stacking or layering many small ablation disks has at several advantages.

An important advantage is that a series of small ablation disks can be still be created even though useful ablation rates require a very high linear scan rate. As discussed in a later section of this application, the linear speed of the focal spot exceeds 1 m/s. Since ablation disks 10 have spiral geometries, the volume of ablation disk 10 can be traced by scanning beam delivery system 220 operating at or near the maximum linear rate. At the same time, the ablation profile can be executed in small increments, so that micron-level precision during the entire ablation process is not necessary. If the entire scanning sequence were performed continuously, as it is in existing femtosecond laser keratomes, the requirements for positioning the tissue with respect to focused laser beam 40 would be onerous. A trade-off in performing many small ablation disk ablation operations is that scanning beam delivery system 220 repeatedly repositions focused laser beam 40, which takes up valuable scan time. In order to minimize the intervals between ablation disk scans, ablation disk 10 characteristic diameter 16 is optimally less than 1 mm.

A second advantage is that the precision tolerance used for positioning consecutive ablation disks 10 can be relaxed relative to the precision tolerance used for positioning of consecutive laser pulses within a particular ablation disk. That is, the error in the positioning of consecutive ablation disks can be much larger than the error in the positioning of consecutive laser pulses within an ablation disks. For example, placement of a particular 1 mm diameter disk may be associated with a lateral tolerance of +/−50 microns, while the placement of two successive laser pulses within that disk may be 3 microns+/−1 micron. The tolerance or precision with which successive laser pulses may be placed partially determines the characteristic surface roughness with which ablation profile 11 can be produced.

Ablation profile 11 is arrived at by the design of the pattern of overlapping ablation disks 10. The tolerance or precision with which successive ablation disks can be placed partially determines the size of the amplitude modulation that ablation profile 11 may have. A relatively relaxed lateral tolerance of +/−50 microns between consecutive ablation disk placements allows for an amplitude modulation of ablation profile 11 comparable with what can be achieved with small spot excimer laser ablations.

The flexibility in designing ablation profiles 11 may be used to perform ablative treatments to remove small areas. In particular, tissue adhesions may be ablated, such as may be created in an unsuccessful manual or incisional maneuver that leaves behind small bits of tissue. Additionally, high order optical errors may be corrected by ablation profiles that require high spatial modulation amplitudes. In other words, the lateral extent of a particular ablation zone can be of small dimensions. Features having lateral dimensions that approximate the diameter of ablative disk 10 may be ablated or removed. Such features may measure as small as 0.5 mm across.

d) Motion Compensation

Ablation is performed on exposed corneal or ocular surfaces that are unconstrained in a preferred embodiment. Motion occurring in the subject eye or cornea be compensated for or otherwise mitigated in order to facilitate an efficacious ablation process.

The human eye during directed fixation of the gaze exhibits three types of motion: (1) tremor, (2) microsaccades, and (3) drifts. During active vision, other motions occur, such as vergence or large scale saccades, etc. (Physiology of the Eye, Dawson, ed. page 663).

The drift contribution is quite slow, taking many seconds, but have relatively large amplitude motions. Drifts may result in several arc-minutes of angular motion, but are easily compensated for by tracking and repositioning scanners between ablation sequences, in which an individual ablation sequence occurs in a burst of time that is on the scale of tens of milliseconds.

Microsaccades occur more rapidly, with high angular speed at irregular intervals of ~1 second. The angular speed is such that the microsaccade will likely cause the ablation sequence to be incomplete or erroneous. However, for the high speed at which the ablation sequences are performed (also tens of milliseconds in duration), the microsaccadic motions will only occasionally cause errors in the ablations, and can be corrected for by repeating zones during which a microsaccade occurs, or by updating the ablation profile algorithm to account for the error. The optical tracking sub-system is used in a preferred embodiment to identify ablation disk 10 sequences in which the positional error exceeds a threshold tolerance value. The ablation profile algorithm is subsequently updated to compensate for the particular incomplete ablation disk flagged as exceeding the threshold tolerance. Preferred processes for performing refractive corrections are outlined in the flow charts in FIG. 6 and FIG. 7. Error checking for such out-of-tolerance ablation disks is explicitly part of a preferred method or process outlined in these flowcharts.

Tremor motion occurs more frequently, though at much smaller amplitudes. The rate of tremor is 30-70 Hz, with amplitudes of up to 20 arc-seconds. The largest amplitude motion corresponds to ~1 micron of lateral movement at the corneal surface. Most tremor individual tremor motions are small enough that they do not have to be compensated or adjusted for. If the integrated motion exceeds a few microns during an ablation disk scanning sequence, the motion is optimally compensated for by subsequent ablations of that area as outlined in the preceding paragraph.

Large scale eye motions, such as non-fixated saccades, or voluntary or involuntary change of gaze or eye positions will result in the treatment being temporarily or permanently halted.

The primary reason for creating an ablation profile 11 by a series of discrete ablation disks 10, rather than by continuously tracking and compensating for relative motion is that the linear speed of the focused laser beam 40 linear speed and the laser repetition rate are very high. These high rates exceed practical limits associated with optical tracking, micropositioning and data processing. The present invention handles these challenges in a novel way through the step-wise fabrication of discrete ablation disk 10 features sized to avoid most eye motions. Errors in ablation disk 10 fabrication are dynamically updated in the ablation profile algorithm.

For example, in an optimally sized photodisruption event 46 depicted in FIG. 8B, the resulting ablation feature size in corneal tissue may measure approximately 2 microns in lateral extent. If the entire ablation sequence to produce a refractive change were performed in a continuous scan, the lateral optical tracking and motion compensation requirement to maintain good registration of the ablation during scanning would require an approximately 2 micron tolerance on tracking and positioning accuracy. This requirement would make any ablation mode difficult and inaccurate.

1) Error Correction

In the present invention, the ablation process requires precise positioning of both consecutive laser shots and the placement of consecutive ablation disks. The size of an individual laser shot ablation is on the micron scale. Fabrication of ablation profiles requires that the tissue removed in such a way that minimal amount of incompletely ablated material lies between consecutive laser shots, and also between consecutive scan lines.

Saccadic or other eye motions may cause relative motion between the focused laser beam 40 and a particular target tissue location. If the number of incomplete, interrupted or erroneous ablation sequences accumulated exceeds a tolerable value, the ablative process can be paused or halted to correct conditions causing unacceptable relative motion of the eye. Low patient compliance or inadequate fixation may cause such motion.

Position errors above a critical size are detected by the optical tracking and axial position sensing functions of the invention. If motion exceeding an allowed tolerance value is detected during a particular ablation sequence, the position and parameters associated with the particular ablation disk scan sequence are used to dynamically update the calculated ablation profile algorithm. The algorithm is update to successfully ablate the region or zone in which the position error occurred, or to compensate for the unsuccessful ablation by adjusting other aspects of the ablation profile algorithm. Incomplete or erroneous ablation disk sequences can be repeated, ignored, or overlaid with subsequent ablation disks.

As an example consider a series of ablation disks with sequence numbers presenting by integers n, m and p. Following the unsuccessful completion of a particular ablation disk number [n], the next planned disk [n+1] may be executed as planned, and the unsuccessful disk ablation [n] repeated before proceeding to disk [n+2]. The pattern of disk ablations is then resumed until the final disk ablation N is reached. Alternatively, the error in disk number [n] may be noted, and several planned disks [n+1] through [n+m] completed. Then, using an adjusted ablation pattern, the volume of tissue at the location of the originally planned disk [n] is removed in a sequence of ablation disk [n+m+1] through [n+m+p]. After this detour in ablation sequence, the original remaining disks beyond number [n+m] are completed.

2) Mechanism for Motion Compensation

Motion compensation during ablation occurs as a result of optical tracking of lateral relative motion and optical sensing or ranging of one or more points on the corneal surface in the axial or depth direction. Referring back to FIG. 1, lateral position optical tracking information obtained through tracking digital cameras 250 may be used to re-direct the internal scanning elements of scanning beam delivery system 220 relative to focused laser beam 40. Alternatively registration platen 120 may be re-positioned relative to focused laser beam 40, thereby translating the position of the non-planar posterior flap surface 112 relative to focused laser beam 40. In an alternative embodiment, both corrections may be applied to optimize the motion compensation response. Axial position information obtained by axial position sensing module 240 may be used to re-direct the internal translating elements of focusing optics module 230 relative to the non-planar posterior flap surface 112.

3) Optical Tracking

FIG. 4D shows a side view of a representative image acquisition step. Scattered illumination rays 60 originating from the surgical field are used by an image processing subsystem in processor 270 (from FIG. 1) to analyze the relative lateral position of the laser optical axis with respect to the cornea.

In an alternative embodiment, high bandwidth tracking allows for tracking, re-positioning and error tracking at speeds exceeding the frequency of the eye, known to be less than 70 Hz. The preferable bandwidth of the tracker enabling individual tremor tracking optimally follows approximately the Norquist statistical criteria for signal sampling. Therefore the desired bandwidth of a suitable tracking system optimally exceeds approximately 250 Hz. For example, the iView X Hi-Speed system from SensoMotoric Instruments GmbH has an adequate maximum acquisition rate of 1250 Hz. A custom image processor is efficacious to achieve the real-time bandwidth requirement for continuous positioning correction.

4) Axial Position Sensing

Tracking of lateral relative motion is performed in a preferred embodiment of the invention using digital image capture, image processing, and image registration. A separate requirement for the present invention is precise tracking of the axial position of the target ablation surfaces with respect to the position of the focus of laser beam 40. A preferred method for measuring and controlling the position of the laser focus is a confocal optical arrangement. A probe optical beam is focused at a point or points on the target surface using focusing optics module 230. Scattered or reflected light from the target surface is re-imaged by focusing optics module 230 and redirected by a beamsplitter onto a photo detector in axial position sensing module 240. The photodetector signal is a maximum when the target tissue surface is located within the depth of focus of this confocal optical arrangement. The photodetector signal may be advantageously used to modulate the focusing power of the ablating ultrashort pulsed laser beam by suitably actuating optical elements of focusing optics module 230.

The focusing power of focusing optics module 230 is arranged to provide appropriate axial depth or z-position sensitivity. Optimally, the depth of focus is set to equal or exceed the precision requirements for optimal an ultrashort pulsed laser tissue interaction, namely surface ablation. The resulting confocal axial sensitivity is then equal to or smaller than the Rayleigh range of the ultrashort pulsed focused beam, which is optimally 3 microns or smaller. The confocal arrangement is similar to many used in confocal microscopy and related techniques.

In an alternative embodiment, a confocal arrangement may be used in combination with a wavelength shift in the probe light beam. Autofluorescence or fluorescence from an contrast agent applied to the target tissue surface provides the detected signal collected from the target tissue surface. As is well known in the art, wavelength shifting of confocally collected probe light is advantageous due to the non-linear dependence of the wavelength conversion on the probe beam intensity. A confocal arrangement with wavelength shifting advantageously increases the sensitivity of the dependence of the optical signal on the axial position.

FIG. 4E shows a side view of the acquisition of a confocal optical signal which locates the z-position or depth position of the focused laser beam relative to the target tissue surface. Confocal volume 71 produces optical radiation that is collected as confocal image beam 70 and relayed to detectors in axial position sensing module 240 (from FIG. 1.)

5) Timing Considerations

Tremor motion amplitude is sufficiently small that conventional video frame rate eye trackers may be used in an alternative embodiment. Although tremor motion occurs at frequencies exceeding typical bandwidths of video frame rate eye tracking systems, the invention may be advantageously used to create ablation disks without correction of motion during each ablation disk sequence, as previously described. In one embodiment, conventional video frame rate bandwidth trackers (25-30 frames/sec) are used in parallel to the ablation disk sequences.

In one embodiment, time intervals between ablation sequences are included in the ablation process to allow for: (i) determination by image-based tracking of the lateral position of the target tissue surface with respect to the laser optical axis; (ii) determination of the axial or depth position of the target tissue surface, most optimally by a sensitive confocal beam detecting the interface between the tissue surface and air, most optimally in a non-ablated region of the cornea, and potentially at multiple sites, (iii) removal of ablation debris by a burst or continuous purge fluid jet directed at or near the ablation site, (iv) an optional process step of hydrating the corneal surface by a mist, aerosol spray or hydration fluid jet. In a preferred embodiment, the features tracked by the lateral image tracking function are fiduciary marks created using the invention in a previous step. Fiduciary mark creation is described below.

In another embodiment, conventional trackers are used, but the tracking occurs at the end of each ablation disk sequence, and the ablation disk sequences lengths are designed to match the tracking speeds. In order to execute a surgical procedure as rapidly as possible, individual ablation disks are scanned with approximate scan duration times corresponding to video frame rates. Timing intervals between consecutive ablation disk sequences are optimally small in comparison to the time to complete a single ablation disk scan sequence. For example, a 25 fps (frames per second) conventional video tracker may be used to acquire images at 40 millisecond (msec) intervals with an image acquisition window width of 5 msec, and a re-positioning window width of 5 msec, with ablation sequences lasting 30 msec. In this example, 10 msec total is allowed for ablation assist processes (described below), if those processes are timed to occur between ablation sequences. The relatively short 5 msec repositioning window may be used to place the scanners into position assuming no motion during the acquisition time. If a positioning error result during the ablation disk creation step, the particular ablation disk may either be halted or allowed to complete, and the position of the erroneous ablation recorded and folded into the prescription for the remaining ablation sequences. A reasonable duty factor for ablation disk creation process of 75% is thus achieved, allowing for the bulk of the total laser procedure time to be dedicated to actual tissue ablation. The repositioning and acquisition times are optimally only a fraction of the "on time" of the laser ablation sequences to allow for the most rapid procedure times.

Axial position sensing module 240 operates in parallel to the lateral eye tracking function. The timing of axial sensing may advantageous be performed in a similar manner as the eye tracking function. Axial position sensing is important because the position of the laser focus is optimally be axially with a precision greater than the depth of focus of the laser beam, which optimally is less than 10 microns, and is more optimally less than 2 microns.

6) Fiducial Marks for Optical Tracking

In excimer laser treatments known in the art, lateral tracking of the iris or pupil is commonly used to control an excimer laser beam or halt the excimer laser beam if the relative motion exceeds a threshold value. In a preferred embodiment of the present invention, the reference points and features to be optically tracked are fiducial marks laser cut into the cornea. Laser-cut fiducial marks may be advantageously impregnated with biocompatible contrast agents to improve the performance of the optical tracking function. Laser-cut fiducial marks are described in detail below.

In an alternative embodiment, un-ablated and un-cut surfaces of the cornea may be used as reference features for the optical tracking function.

In a preferred embodiment, the optical paths used for lateral tracking and z-position tracking are shared by the laser beam focusing and scanning objective lens. Alternative embodiments may use a parallel optical path or paths, as would be clear to one skilled in the art.

e) Theory of Operation—Ablation

The present invention operates by producing controlled optical breakdown events in ocular tissue. Each optical breakdown event results in a set of secondary phenomena known as photodisruptions. The phenomena of photodisruptions include: shock wave generation, shock wave propagation, localized tissue vaporization, gas vapor bubble expansion, and gas bubble cavitation. These are well-known physical processes that have been advantageously used in other laser keratomes. Photodisruptions act in a small volume highly localized to the location of the optical breakdown. Ultrashort pulse photodisruption events in ocular tissue are typically 1-100 microns in extent, depending on the particular laser parameters and tissue properties involved.

As is well known in the art, femtosecond and picosecond laser keratomes use photodisruption to produce incisions in ocular tissue such as cornea. Both an incisional mode and an ablative mode are realized in the present invention. However, a novel aspect of the invention is to perform refractive surgery by direct ablation of tissue using ultrashort pulsed laser photodisruption at or near a tissue surface. Ablation is not used by ultrashort pulsed laser keratomes known in the prior art.

Enabling features for the ablative mode of the invention include: (i) high bandwidth lateral optical tracking; (ii) depth-sensitive optical tracking of the axial position of the target tissue; (iii) ablation profile patterns based on overlays of ablation disk scan patterns, said ablation disk scan patterns being sufficiently rapidly performed so as to in the main avoid pattern disruption by the larger amplitude natural motions of the eye; (iv) fabrication of fiducial marks on or in the cornea to enable lateral optical tracking independent of the eye anatomy and unaffected by the ablation process; and (v) apparatus for holding, registering and conditioning a corneal flap to allow ablation of the posterior surface of the flap. Various embodiments of the invention may use some or all of these enabling features in combination.

A description of the theory of ablative operation is therefore shown below.

1) Ablation Volumes

Optical breakdown and photodisruption are arranged to occur at or near a tissue surface exposed to air and to the impinging focused laser beam 40. Material is ejected from the free surfaces targeted by impinging focused laser beam 40. Repeated scanned patterns of laser pulses may remove a specific volume of tissue to create a refractive effect.

The zone of tissue affected by a superficial application of an optimal pulse is deeper than the nanosecond excimer pulses used in commercial refractive laser keratomes. Additionally, the lateral zone of ablated tissue associated with a single laser pulse is measured in a few microns rather than the approximately 1 millimeter width associated with refractive lasers such as are used in so-called flying spot excimer lasers. Lateral in this sense refers to the planar dimensions parallel to the corneal surface. A zone of tissue ablated through optical breakdown and associated processes by such a pulse would optimally be a volume of a few microns across and 1 micron or less deep. It is advantageous that the depth of an individual pulse or application of pulses at a particular surface be small compared to the optical power associated with the removal of a layer of corneal tissue of the same thickness. A beneficial pulse may produce an individual ablation feature measuring 1 micron deep with a lateral radius of 1 micron, with a volume of approximately 3 cubic microns.

In order to make useful the small ablation features produced by the invention, a large number of pulses are preferably rapidly applied in a short time to remove a useful volume of tissue. To estimate the number of laser shots to complete a clinical procedure, consider the well-known Munnerlyn formula predicting the size of a lenticular section of cornea to be preferably removed in order to make a refractive correction. For a myopic correction, a lenticular volume of approximately $$\sim \tfrac{1}{3} * (R \text{ zone})^2 * CT$$

is to be removed. R zone is the radius of the optical zone and CT is the central and thickest part of the lenticular piece of tissue to be removed. For a relatively large correction of 10 diopters, typical exemplary values may be used: R zone=3 mm; CT=100 microns.

The resulting lenticular volume to be removed in this example is approximately $3 \times 10^{\wedge}8$ cubic microns. If the pulses are assumed to ablate this volume with 100% efficiency, using an approximate value of 3 cubic microns/laser shot for the volume ablated in a single pulse, an estimated $1 \times 10^{\wedge}8$ individual pulses would be used. However, in reality a significant overlap of individual pulses is preferable to produce a smooth ablation profile. An effective ablation efficiency of 30% or less relative to the theoretical ablation efficiency associated with the single pulse ablation volume value used above. Therefore, the same volumetric tissue removal requirement for an exemplary 10 diopter correction above may require as many as $3 \times 10^{\wedge}8$ individual pulses. The present invention may advantageously complete the ablation of this volume in a clinically reasonable time, for example, 100 seconds. The approximate laser repetition rate estimated in this example is then approximately 3 MHz.

Some incisional femtosecond laser keratomes presently marketed achieve such high laser repetition rates. For example, the Ziemer LDV system (Ziemer Ophthalmic Systems AG) operates at up to 2 MHz, though at much lower average power than the present invention. The LDV maximum average power is approximately 100 nanoJoules*2 MHz=200 milliWatts. The LDV and other laser keratomes operate only in an incisional mode.

2) Scanning Performance

Another aspect of the invention is the requirement for high beam scanning rates. Using the example parameters from above, the estimated lateral separation of adjacent laser focal spots is optimally approximately 1 micron. A typical linear rate of scanning that accurately places consecutive laser spots at this separation requires a well-controlled linear speed of 3 m/s, though rates between 1 and 10 m/s may be advantageously used.

This high rate of linear scanning may be performed in several ways. The most advantageous way is the use of a large field high numerical aperture F-theta scanning objective lens. This method is well known in the art of laser scanning, and is commonly used in femtosecond laser keratomes. The F-theta lens is a laser scanning lens in which the image height, or rather the lateral location of the focal spot, is proportional to the product of the laser beam entrance angle with respect to the optical axis (theta, or $\theta$) and the lens focal length F. That is, the spot position is proportional to the product $F*\theta$, rather than the usual value for conventional lenses of $F*\tan\theta$. The linear scan rate for such an F-theta is then linearly dependent on the angular speed of the incoming beam, rather than the usual dependence of angular scan rate for an ordinary lens of the quantity $d/dt[\tan\theta]$. This is generally accomplished with appropriate lens design that includes the correct amount of optical distortion in the lens to produce the $F*\theta$ dependence of the focal spot position.

$$\text{linear scan speed}\sim\omega*F$$

where $\omega=d\theta/dt$ is the angular sweep speed of the input laser beam

Galvanometric (galvo) motor rotation rates as 1000 radians/sec are preferable for high linear spot speeds.

The timing intervals between scans of consecutive ablation disks 10 may require duty cycle factors of 75% or more.

To achieve a high angular rate, a high torque and angular speed galvanometric or other electromechanical motor devices are used to drive relatively small diameter mirrors, optimally 1 cm diameter or smaller. Optical processing module 210 conditions the laser beam to match the beam diameter and beam divergence to properly fit on the small deflection mirrors in scanning beam delivery system 220. The angularly deflected, small diameter beam is then expanded in an optical telescope or equivalent in focusing optics module 230 and launched into a high numerical aperture (NA) F-theta scan lens, or into a similar field scanning lens. The angle of the input beam with respect to the lens optical axis determines the position of the focal spot, and therefore the incision cutting point or ablation point of the femtosecond beam.

3) Free Surface for Ablation

There is a requirement in femtosecond laser keratomes known in the art, and also in the present invention, that the scanned laser pulses are placed regularly and continuously so that scan spots and scan lines can be laid precisely together. Further, the laser scans are preferably rapid enough that clinical procedures can be performed in an acceptable amount of time. The preferred method for producing scans both rapidly and with high precision uses a spiral scan. Spiral scans allow the angular scanning speed to be continuously high, while the small increment in the spiral radius allows for good control of the placement of consecutive scanning lines. The latter point is important because errors in precision due to the scanning or motion that occurs add up to degrade the incisional quality. Incisional femtosecond laser keratomes use mechanical fixation and an applanation optic to maintain precise registration between the cornea and the scanning optical axis. Femtosecond laser keratomes are frequently assisted by the use of a low vacuum or suction limbal suction ring that temporarily attaches by suction to the corneal periphery or the limbus. In these keratomes, incisions are created in the corneal stroma, with the laser beam passing through an applanating contact optic. The contact glass serves as a precision reference surface for the scanned laser beam, and also immobilizes the cornea. Typically, the applanating contact optic is used to maintain lateral and axis stability of the cornea with respect to the incident cutting laser beam.

While applanation with a applanating contact optic works well for incisional procedures, performing ultrashort pulsed laser ablation with an applanating contact optic is problematic. Material ablated at the surface of the cornea or other ocular tissue may be trapped between the ablation zone and the applanating optic. The result would be a combination of optical blocking of subsequent laser pulses by trapped debris, adhesion of debris to the target tissue/substrate, and deposition of unwanted heat back into the bulk material from trapped ablation ejecta. Ablation is optimally performed with the target tissue surface to exposed or free.

The invention may also be used partly or wholly without requiring the limbal suction fixation rings often employed by femtosecond laser keratomes known in the art.

On the other hand, in performing ablation with ultra-violet (UV) wavelength lasers, such as the excimer lasers used in LASIK procedures, applanation of the cornea is not necessary. Applanation is not necessary in UV ablation of the cornea because the control of the z-position of the laser beam with respect to the target tissue surface is not particularly important. The ablating UV beam is not focused, but is rather collimated. Tissue ablation performed with these lasers occurs independently of the axial location of the ablation surface with respect to the laser beam. Ablation by such a laser beam occurs wherever the beam intersects the target absorbing material, viz., corneal stroma. This is because the ablation occurs due to the linear absorption of the collimated beam, and does not depend on a tightly converging beam, as is arranged in the present invention. Put another way, an ablating UV beam propagates until it strikes the cornea, where it is strongly absorbed and creates ablation of a particular depth that depends linearly on the fluence of the incident beam.

In order to produce tissue ablation with high precision and limited collateral damage, the size of an individual ablation event is optimally of extent from one to several microns in size. This is achieved in the present invention with tightly focused ultrashort laser pulses applied at or near a surface to be ablated, with parameters chosen to produce optical breakdown at or just below the target surface.

4) Wavelength

Transparency of the target tissue is the principal concern in choosing a wavelength for the invention. The transparency window of ocular tissue from approximately 700 nm to 1100 nm is an acceptable range. The invention preferentially uses wavelengths between 1000 nm and 1100 nm.

5) Pulse Duration

As is known in the art, photodisruption of ocular tissue by ultrashort pulsed lasers may usefully be performed below pulse durations of 10 picoseconds. Pulse durations of less than about 1 picosecond optimally produce deterministic and localized photodisruptions. Pulse durations of about less than 50 femtoseconds are unnecessarily difficult to manage in optical designs. The invention therefore preferably uses pulse durations less than 1 picosecond and greater than 50 femtoseconds.

6) Focusing

As previously described, ultrashort pulsed laser beams may be advantageously arranged to produce optical breakdown and photodisruption of tissue. Properly chosen parameters localize effects immediately proximate to the focus of the laser beam. A focused scanning femtosecond beam impinging on a transparent tissue does not produce any absorption in target tissue until the fluence exceeds a threshold value. The threshold value for optical breakdown is controlled by the focusing properties of the beam, as well as by controlling the laser beam pulse parameters. This allows for the unique interaction properties exploited by femtosecond laser keratomes known in the art, such as the ability to produce localized effects at a precise point in three dimensions, without affecting surrounding tissue.

Control of the focal position with respect to the target location is optimally precisely controlled, preferably on the scale of one micron. This is usually achieved through the use of an applanating contact optic. With the present invention, an applanating contact optic may or may not be used in the incisional mode. In the ablation mode, no applanation glass is used. Ablation is performed by the invention upon exposed ocular tissue or corneal stroma surfaces.

Therefore, the invention preferably corrects or compensates for relative motion of the eye and target tissue surfaces with respect to focused laser beam 40 in three dimensions. The motion compensation requirements are determined in part by the beam focus requirements. Typically, focus depth of a laser beam is described by the Rayleigh range parameter, which is defined as the axial distance over which the beam diameter increases from the minimum value at the laser focus by a factor that results in a doubling of the spot area. For a Gaussian laser beam, this is related to the focal spot radius:

$$Z_{Rayleigh} = pi*(\text{focal spot radius})^2/\text{lambda}$$

For an advantageously sized spot diameter of 1.5 microns and a wavelength of 1.064 nm, the Rayleigh range is approximately 1.7 microns. The desired precision in the depth or axial position of the focal spot is related to the Rayleigh range, viz., preferably less than 5 microns and optimally to within 1 micron.

7) Pulse Energy

In the present invention, the preferred extent or length scale of the laser-tissue is between one and several microns. The pulsed energy used per laser is preferably not large in comparison to the optical breakdown threshold in order to achieve this size of tissue interaction. In preferred embodiments, the invention may produce optical breakdown events using pulse energies between 0.1 and 1 microJoules. To limit the feature size of a single laser-tissue interaction, the energy per pulse is optimally less than about 10 times the optical breakdown threshold energy, and as small as practicable. The preferred pulse energy range of the invention is therefore between about 1 and 20 microJoules, and preferably between 1 and 10 microJoules.

8) Average Power

Ablation of corneal tissue, whether using the present invention or some other means, is optimally rapid enough to perform a clinical procedure in a short period of time. Acceptable procedure times for the actual material ablation step are 1 minute or less. To achieve this performance, the high average power ultrashort pulsed laser beam of the invention is optimally scanned at a high linear rate of speed across the target cornea surface(s).

Additionally, using the volumetric ablation rates estimated above, laser source 200 of the invention preferably operates between 1 and 10 MHz, and used between 1 and 10 microJoules per pulse. The invention preferably uses between 1 and 100 Watts of average power, and optimally used between 1 and 10 Watts of average power.

The average power of present invention is between 1 and 2 orders of magnitude higher than is used in femtosecond laser keratomes known in the art. The delivered average power optimal for the direct ablation of a clinically meaningful amount of cornea is significantly higher than would be used to simply incise or cut cornea. The invention may be switched between incisional and ablating modes, enabling a single instrument to create a corneal flap or other incisional feature, and then to ablate tissue to produce the desired refractive effect. In the incisional mode, the invention preferentially uses between 100 milliWatts and 1 Watt of average power.

g) Ablation Assist Features

In the ablative mode of the invention, ablated material may accumulate as debris on surfaces proximate to the target tissue. Such debris may impede the ablation process. The debris is advantageously removed by gas or fluid purging, in a process that is similar to processes well known in the art of laser material processing. In the present invention, the ablation debris is biological tissue rather than metal or other materials commonly removed by air, liquid or other fluidic jet or purging streams known in the art. Purging functionality is integrated into ablation assist arm 50.

An additional process of replacing moisture from the surrounding or underlying tissue may be desirable. A humidity supplying element or a water-aerosolizing element may be employed to continuously direct mist, humidity or vapor at the tissue in order to maintain physiologic humidity. Such an element may consist of a platen surrounding the tissue subject to ablation at a close distance, and may consist of a rigid member with a through hole that allows the laser and other optical beams to reach the corneal tissue. Alternatively, direct contact with a moisturizing surface in contact with the anterior surface of the corneal flap may be used. The moisturing surface may be integrated with registration platen 120, and may consist of a series of irrigation pores or micropores in registration platen 120.

FIG. 4A depicts a side view of cornea 22 with a flap already cut, lifted and reflected with corneal flap anterior surface 25 facing away from the focused laser beam 40. Exposed stromal bed 28 already has a sequence of ablation disk features created, with creation of single ablation disk 10 in process. Single ablation disk 10 is one in a sequence of scanned ablation disks. Ablation assist arm 50 is mounted on a motion control system integrated in the laser console (not shown). Aperture plate 52 contains central aperture 51 that allows focused laser beam 40 to reach corneal stromal bed 28.

FIG. 4B shows a side view of ablation assist arm 50 performing ablation assist processes. Nozzle 52 directs purge fluid 44 onto the local ablation area associated with ablation disk 10. Purge fluid 44 may consist of pressurized air, water, saline, or other fluids or fluids mixture compatible with biological tissue and useful for removing by pressure and direct contact any ablation products. At the same time, or alternatively, at a different time sequence, moisture or mist 42 may be supplied to the corneal tissue by hydration ports 56.

FIG. 4C shows a side view of the repositioning of ablation assist arm 50 from position 58 to subsequent position 59. The repositioning of ablation assist arm 50 occurs in order to ready ablation assist arm 50 for the next ablation disk in the planned sequence. The repositioning occurs under motion control elements which center aperture 51 and other associated ablation assist features of ablation assist arm 50 over the next target tissue location.

Both the purging step and the humidifying step may be performed by the invention at intervals or continuously, depending on the particular ablation parameters. The assist processes of debris purging and hydration may occur in parallel to the ablation sequences, and combinations of sequential and parallel assist steps may be advantageously employed.

h) Posterior Flap Ablation

An alternative embodiment avoids ablation of the exposed stromal bed in favor of ablating the posterior surface of a corneal flap. The flap may be created by incision with the ultrashort pulsed laser, or by mechanical or other means. An advantage of ablating the posterior surface of the flap is that the interior of the globe itself is not exposed to laser radiation. In conventional LASIK or other laser refractive procedures, the corneal stromal bed and the interior of the eye are directly exposed to UV laser radiation. Replacing the UV ablating laser with direct exposure of the eye interior to the high average laser power of the present invention may result in a hazardous exposure of eye structures to thermal or other energy. An advantageous embodiment of the invention is used to perform ablation upon the mechanically reflected and exposed posterior surface of a pre-cut corneal flap. This method avoids harmful radiation or thermal effects from laser exposure to the interior of the eye.

1) Non-Planar Posterior Flap

In an embodiment of the invention, an initial non-planar flap shape is cut in such a way that subsequent ablation of the flap produces a final flap geometry that is planar. A non-planar flap may be cut by the incisional mode of the present invention, by a commercially available femtosecond laser keratome, or even by a specialized mechanical blade keratome. Using the incisional mode of the present invention, a circularly symmetric but non-planar flap cut may be made by changing the depth of the focal point continuously and slowly as the spiral cutting of the flap is performed.

FIG. 5A depicts a side view of a cornea that has had a non-planar flap cut by ultrashort pulsed laser incision. The non-planar flap cut contains non-planar posterior flap surface 112 and planar posterior flap surface 110. The non-planar flap cut may be performed with or without the use of the well-known applanating optics described in the art of femtosecond laser keratomes. Peripheral located planar posterior flap surface is parallel to the corneal anterior surface, but non-planar posterior flap surface 112 has a curvature that is not parallel to the corneal surface. Fiduciary marks 36 are produced as in FIG. 8 (described below), but with the incisions being made in the posterior surface of the planar posterior flap surface 110 rather than in stromal bed 116.

2) Registration Platen

In the posterior flap ablation embodiment of the invention, a feature to register, hold and manipulate the flap tissue is preferably used. The feature, referred to as registration platen 120 in FIG. 5B, fixes the posterior surface with respect to the ablating ultrashort pulsed laser beam 40 with a high degree of precision and steadiness.

Registration platen 120 is depicted in FIGS. 5B and 5C. Registration platen 120 performs several functions: (i) to mechanical hold anterior flap surface 25 onto precision registration platen interface; (ii) to provide a means for mechanically translating or rotating the corneal flap in three dimensions to optimize the orientation of non-planar posterior flap surface 112 to the ablating laser beam; (iii) to provide the appropriate level of physiologic hydration to the flap tissue before, during and after the ablation process; and (iv) to provide a laser absorption and thermal sink for the appreciable fraction of incident laser power which passes through the tissue without contributing to the optical breakdown and ablation process.

FIG. 5B shows a side view of the corneal flap of FIG. 5A now affixed to registration platen 120. Registration platen 120 is connected to registration platen actuator module 262 (FIG. 1) and provides precision three-dimensional positioning control to registration platen 120. Registration platen 120 may also in some embodiments have the ability to gimbal or rotate the center of the corneal flap with respect to one or more rotational axes to orient the posterior flap surface with respect to the focused laser beam 40. Registration platen interface 122 of registration platen 120 may be a disposable element. Registration platen interface 122 has a smooth curved surface designed to match a typical human corneal surface. To aid in the mechanical fixation of the corneal flap on registration platen interface 122, manifold 124 of low vacuum level may be integrated into element 122. Manifold 124 may be supplied with low suction force or vacuum from vacuum lines in registration platen 120 connected to the laser system (not shown). Additionally, hydrating features 126 may wick, bleed or flow small amounts of physiologically appropriate fluid such as buffered saline to the flap anterior surface. Hydrating features 126 may be connected to a supply of fluid through a manifold and further connected to a pump or reservoir of fluid in the console (not shown).

The suction force and hydration fluid are supplied by registration platen actuator module 262. The suction force applied by hydration manifold 126 is sufficiently low to release flap in the event of movement.

FIG. 5C illustrates a side view of the laser ablation step in posterior flap ablation. Laser beam 40 is focused and scanned over non-planar posterior flap surface 112. An ablation profile is built up as illustrated before in FIG. 2 and FIG. 3. Registration platen 120 may be used in conjunction with ablation assist arm 50 and ablation assist processes illustrated in FIG. 4.

FIG. 5D shows a side view of ablated posterior flap surface 130 of the posterior flap surface. Initial non-planar posterior flap surface 112 is designed and cut such that ablated posterior flap surface 130 results in a final posterior flap surface that is continuously parallel to the anterior corneal surface.

FIG. 5E shows a side view of the corneal flap after repositioning the flap onto exposed stromal bed 116. The result of the ablation of non-planar posterior flap surface 112 to yield ablated posterior flap surface 130 is a corneal flap of uniform thickness, similar to the flap geometry obtained in conventional microkeratome-generated corneal flaps. Ablated posterior flap surface 130 results in the corneal surface relaxing to a new position, giving rise to a new corneal shape 140 and refractive power. Functionally, this is equivalent to creating a flap, and incising and removing a lenticule of the same shape and volume. It is also equivalent to the stromal bed ablation process outlined in FIG. 4, but is produced with exposing the interior anatomy of the eye directly to the ultrashort pulsed laser beam used for the ablation process.

The control of the depth or axial dimension may be advantageously controlled by translating registration platen 120, by altering the position of focused laser beam 40, or a combination of the two methods for optimal control of the ablation depth in tissue.

In an alternative embodiment, optical tracking is not dynamically used duration ablation, since the position of non-planar posterior flap surface 112 can be maintained and controlled in three dimensions by movement of registration platen 120 with respect to focus laser beam 40, once the correct initial position of the flap has been obtained. Optical tracking may be used to obtain the initial correct position of the flap in this alternative embodiment.

It should be clear to the reader that other pre-cut flap geometries and ablation profiles 11 may be advantageously used by the invention. For example, an ablation profile of the posterior flap surface may result in a flap that is not planar after the ablation process is complete.

In an alternative embodiment, combined curvatures ablated in both exposed stromal bed 116 and in non-planar posterior surface 112 to create a desired refractive change.

In yet another alternative embodiment, ablation of non-planar posterior surface 112 is arranged to produce ablation profiles to perform myopic or hyperopic corrections.

In yet another alternative embodiment, ablation of non-planar posterior surface 112 is arranged to produce non-circularly symmetric ablation profiles to perform astigmatic corrections, or to create other non-spherical or higher order refractive error corrections.

3) High Average Power Ablation

The high average power to ablate corneal and ocular tissue in an acceptably short time may exceed safe limits for retinal and thermal exposures. For example, an optimal 10 W average power beam of femtosecond laser pulses used a preferred embodiment of the invention to ablate tissue for a clinically acceptable duration of 60 seconds results in an approximate 600 J laser energy exposure to the interior of the eye. Such an exposure is obviously unacceptable. The use of posterior flap surface ablation avoids such exposures. In a preferred embodiment, high average power ablation is enabled by this method and device because the total exposure of laser power or energy in direct stromal ablation would otherwise represent a hazardous laser radiation exposure to the subject eye.

i) Exemplary Process Flows

One embodiment of the invention may be used to perform a corneal refractive procedure that resembles a LASIK procedure. In a first step, the invention is used to produce a conventional corneal flap. Alternatively, other instruments, including mechanical blade based microkeratomes, may be used to create the flap. In a second step, an ablative portion of the corneal refractive procedure is replaced with the ablative mode of present invention. An ablation profile 11 is performed as previously described. Ablation profile 11 is constructed to resembled the ablation nomograms produced by an excimer laser ablation, for example, as may be used in a so-called "flying spot" excimer laser LASIK procedure. In analogy to the excimer procedure, each flying spot may be considered as a single spiral scanned ablation disk 10 previously described. The ablation disk features 10 are placed with the aid of a high bandwidth three dimensional optical tracking apparatus, which in a preferred embodiment uses a set of laser cut and contrast-agent dyed fiduciary marks to serve as the optical contrast tracking features.

FIG. 6 presents a detailed procedure flow for this embodiment.

Another embodiment of the invention is the performance of a corneal refractive procedure using the previously described technique of posterior flap ablation.

FIG. 7 presents a detailed procedure flow for this embodiment.

j) Theory of Operation—Incisions

Conventional ultrashort pulsed laser keratome incisions, such as corneal flaps, lamellar keratoplasties, penetrating keratoplasties, relaxing incisions, and other incision shapes may obviously be realized by the invention.

The incisional mode of the present invention is similar to that of commercially available femtosecond laser keratomes.

In a preferred embodiment, incisions may be created without using an applanating contact optic, through the use of optical tracking oriented by laser-cut fiduciary marks.

In an alternate embodiment, well known methods in the art of femtosecond laser keratomes may be used to create incisions. These methods include, but are not limited to: use of a means of mechanical or suction fixation of the eye; use of a contact optic to applanate the eye; and the use of an applanation optic to serve as a reference surface for focused laser beam 40.

k) Fiduciary Marks

Optical tracking is optimally performed by imaging features having good optical contrast and that represent a fixed reference surface locates the target tracking object is located in two or more dimensionals of position and rotational space. In refractive excimer laser system and ophthalmic diagnostic devices known in the art, the pupil of the eye is often used as a reference. However, the pupil is not a fixed reference. The pupil can dialate or move under accommodation, other ocular motions or under the influence of intraocular pressure changes.

Retinal trackers are used for some purposes, though they cannot be used to track or control the corneal surfaces in the present invention, since there is a significant separation and possible deformation between the front and back portions of the eye.

A preferred method is to use a feature in the anterior chamber, and more preferably to use the cornea itself. However, the cornea is transparent and offers little optical contrast. The corneal surface may be manually marked using a surgical marking pen with an ink, dye or stain. It is advantageous, however, to create optical marks or features with a well-defined spatial relationship to the visual axis of the patient's eye. It is further advantageous to create such marks with a well-defined feature size, geometry and contrast because of the high precision preferred for the tracking and motion correction to precisely perform the incision and ablation maneuvers of the present invention.

The present invention combines several elements to create high contrast, precision features for optical tracking referred to as fiduciary marks. The first element is the common method of directing the patient to gaze fixedly at a known object in order to establish fixation of the eye. The second element is visualization of the patient eye by the physician or operator through viewing optics or a relayed video image of the eye to verify proper fixation of the patient gaze. The third element is the cutting of predefined incisional patterns using the ultrashort pulsed laser into or onto the cornea. The forth element is the staining, dyeing or marking of the surfaces containing the incisions by the application of appropriate contrast agent or agents. The fifth element is the subsequent washing or rinsing of the tissue surface containing incisions to remove excess contrast agent.

Fiduciary marks may be created in a single sequence with the creation of other incisions, such as flap generation. Fiduciary marks may also be created separately from other cuts. Fiduciary marks may be located on the posterior surface of a corneal flap, on the stromal bed underneath the flap, or may be on the anterior surface of the otherwise uncut cornea.

The fiduciary mark cutting itself optimally occurs very rapidly so that at the moment of best patient fixation, the pattern of cuts is laid in without motion of the eye. Once the fiduciary mark cuts have been produced, the tissue where the fiduciary mark cuts are located is accessed, either directly at the corneal surface or by lifting a ultrashort pulsed laser flap cut. The contrast agent is applied by irrigation, wiping or other means. Excess contrast agent is washed or dabbed away to leave a significant amount of agent trapped, stained, bound or otherwise localized in the array of incisions. The agents may be simple biocompatible dyes, such as Gentian violent, indocyanine green (IDG), brilliant blue G, Bengal rose. The agents may also be ophthalmic fluorescent dyes, such as fluorescein or rhodamine based dyes. The agents may also be biocompatible optical scattering agents, biodegradable agents, biocompatible pigments such as melanins.

Importantly, fiduciary marks are created with dimensions that are large enough to be advantageously impregnated with the applied contrast agent, but small enough that the agent is easily dispersed over time. The dimensions are also advantageously chosen to minimize effects on human vision. In particular, the widths and depths of the marks are optimally small. Preferred fiduciary mark kerf widths are between 1 and 30 microns, and preferably between 5 and 15 microns. Preferred fiduciary mark depths are between 10 and 100 microns, and preferably between 20 and 50 microns.

FIG. 8 illustrates the creation of femtosecond laser cut fiduciary marks 32 used to optically track the lateral position of the cornea with respect to a subsequent femtosecond laser ablation process step. All sequences of FIG. 8 are shown with the anterior chamber of the eye and cornea shown in cross section.

FIG. 8A shows a side view of cornea 22, the orientation of the anterior segment anatomy with respect to the focused laser beam 40, and the incisional paths associated with a flap cut and the creation of fiduciary marks 32. Phakic lens 98 is attached to ciliary processes 96 by zonule fibers 93. Iris structure 91 anterior to the lens 98 creates pupil 97 at the posterior of humor-filled anterior chamber 95. Above these structures, cornea 22 is connected to sclera 94 by the limbus 92. The beam 40 is shown scanning across planned flap incision plane 82, having partially created flap incision 80. A separate scanning sequence has produced side cut 84 to allow access to the flap with surgical hand instruments.

In FIG. 8B, an expanded side view from FIG. 8A is shown. The focal position of the moving focused laser beam 40 results in individual and rapid photodisruption events 46. Photodisruptions 46 are created by the optical breakdown that the femtosecond laser beam intensity produces. Secondary processes from the optical breakdown such as acoustic shock wave generation and propagation, cavitation bubble formation and oscillation and eventual localized tissue vaporization produce the micro-surgical effect of photodisruption in the same manner as is known in the art associated with incisional femtosecond laser keratomes. Side cut 84 is shown as a hashed line, as are already-cut flap incision 80 and vertical fiduciary mark features 32. Planned flap incision 82 is shown as a dashed line. Incision 80, side cut 84, and fiduciary cuts 32 may be cut using the invention in combination with the well-known applanation optics described in the prior art of femtosecond laser keratomes. Alternatively, incision 80, side cut 84, and fiduciary cuts 32 may be cut without an applanating optic using an eye motion compensation system based on a lateral eye-tracking and z-position confocal sensor.

FIG. 8C shows an expanded side view of FIG. 8B after the flap (not shown) has been lifted from side cut 26 and exposing the interior of cornea 22. Application of a contrast agent 102 is made on the exposed cornea interior using applicator 100. Fiduciary marks 30 have been dyed, marked or stained with the contrast agent 102. Excess contrast agent 101 may be removed with irrigation or application of an absorbent wipe.

In FIG. 8D a top view is shown of the cornea in which the fiduciary mark dyeing or staining process steps have been completed and fiduciary marks 30 are visible with high optical contrast against the stromal bed 28.

In another embodiment, fiduciary marks are created on the portion of the cornea outside of planned femtosecond cut or ablation zones in the process flow of FIG. 6, and as shown in FIG. 3 and FIG. 4.

In another embodiment, fiduciary marks are created on posterior flap surface outside of planned femtosecond cut or ablation zones in the process flow of FIG. 7, and as shown in FIG. 5.

l) Combined Modes

The invention may combine the use of fiduciary mark features, incisional modality and ablative modality. For example, the invention may be used to cut a corneal flap and then be used to subsequently perform an ablative refractive procedure.

The invention may be used to perform incisional operations with or without the use of applanating contact optic. If an applanating contact optics is used, fiduciary marks may be initially created, then marked with a dye or contrast agent, then utilized by the eye tracking subsystem to correct for eye motion, with or without subsequent applanation. If applanation is not used, fiduciary marks may still be created. In either of these two cases, centration of the laser beam with respect to the patient visual axis may be performed by instructing the patient to fixate at an optical target, which may be corrected for the particular patient's refraction. The physician may use optical means for verifying proper fixation prior to initiating the laser scan sequence that creates the fiduciary marks. The fiduciary mark scans may be performed very rapidly so that the marks are created at precisely the correct moment of best fixation. This step may be important in that the fiduciary marks provide information that the invention uses to create refractive incisional and ablative features. These features would result in refractive errors if the fiduciary marks used to center them resulted in a decentering error. An additional step of verifying the centration of the fiduciary marks may be used in which the physician visualizes the patient eye and the selectively dye-stained fiduciary marks and uses the user-interface to record in the system software an appropriate offset value.

In another embodiment, the method of producing optically trackable fiduciary marks in the cornea may be performed to enable completely distinct subsequent procedures or techniques that are neither refractive surgery or ultrashort pulsed laser procedures. In other words, the creations of fiduciary marks may be used for other surgical or diagnostic procedures for which the determination of the visual axis of this eye is important.

m) Other Embodiments

1) Finishing Cuts

Side effects associated with the use of femtosecond laser keratomes are knownt to include "transient light sensitivity syndrome", and diffuse lamellar keratitis. It has been reported that these and other surgical complications may be associated the use of high energy pulses.

The present invention may be used advantageously to first perform ablative refractive procedure using relatively high energy pulses, and then to complete the procedure by ablating the final layers of tissue removed using substantially lower laser energy. The ablation efficiency of the overall surgical procedure is not substantially affected because most of the tissue ablation occurs at high laser energies. Unwanted tissue damage or tissue effects performed at high energy are avoided because the final thickness of tissue removed was performed at a lower energy. Such an approach is similar to how mechanical machining of a material surface is performed with conventional steel tools. I therefore refer to the use of the present invention to perform final ablations using low pulse energies as "finishing cuts". Finishing cuts performed in this way have other advantages, including creating intrinsically smoother surfaces than would occur if high pulse energies were used.

2) Topographically Planned Ablation

In an alternative embodiment, the procedure described in FIG. 5 and FIG. 7 may be performed without active optical tracking or axial position sensing. Topographic mapping of the cornea may be used as input to the determination of the ablation profile algorithm. After an initial step in positioning a pre-cut flap on registration platen 120 with respect to focused laser beam 40, the invention may execute the ablation profile algorithm "blindly", relying on the known position of registration platen and the previous knowledge of the corneal topography. Similar approaches will be obvious to one skilled in the art. For example, a similar mapping of the cornea may be performed using wavefront analyzers and used as input information for the determination of the ablation algorithm.

3) Lenticules and Tissue Adhesions

As in known in the art, femtosecond laser keratomes may be used to cut a stromal lenticule to be extracted from the cornea to produce a refractive change. The present invention may also be used to simultaneously cut a flap and a stromal lenticule to be extracted from the cornea through the flap, In the lenticule procedure as performed presently by femtosecond laser keratomes, a small amounts of adherent tissue resulting from the mechanical removal of the lenticule can result in significant degradation of the visual outcome. The present invention may be used to follow up the incision and removal of the lenticule with a custom ablation of the tissue tags or adherent tissue. This approach enables the removal of unwanted tissue tags, stromal fragments or other small scale defects in cornea or corneal stroma, that cannot be performed by the surgeon with sufficient precision or reliability.

Conclusions, Ramifications and Scope of Invention

Thus the reader will see that the laser apparatus of the invention provides a means of producing corneal refractive surgery through direct ablation of ocular tissue. The invention may also be used to perform corneal incisions in the fashion of other ultrashort pulsed laser keratomes. Optical tracking and laser-cut fiduciary marks in ocular tissue assist in the ablative performance of the laser apparatus. The reader will also see that the method of producing refractive corrections allows for the advantageous use of a single instrument, eliminating the need for two separate surgical instruments.

The description of the invention above contains many examples and specifications for clarity. These examples and specifications are not intended to limit the scope of the invention. For example, in the ablating modality, ablation features other than circular planar disks may be employed, such as planar annular rings, non-planar disks, or non-planar thin strips. In another example, two different pulse width laser beams may be used to produce the incisional cuts and the ablative tissue removal in order to advantageously operate the laser instrument in different pulse regimes.

The present invention is also a general method for ablation of ocular tissues. For example, non-corneal tissue may be ablated and the optical tracking and high speed ultrashort pulsed laser beam may be advantageously used to produce ablation of ocular tissue such as sclera for the creation of sclerotomy features in the treatment of glaucoma. In another example, the ablative mode may be used for the ablation and removal of lens tissue for the treatment of cataracts or presbyopia.

Another alternative use of the invention may be the ablative removal of dermal tissue for cosmetic or dermatologic treatments such as skin cancer treatments.

The present invention allows high power ultrashort pulsed laser ablation of tissue that may exhibit uncompensated or uncontrolled small motions with respect to the ablating laser beam. The present invention represents a general method for ultrashort pulsed laser surface milling of a surface that may move or change during the ablation process.

While my above description contains many specificities, these should not be construed as limitations on the scope of the invention, but rather as an exemplification of preferred embodiments thereof. For example, curved or flat applanation optics commonly used in femtosecond laser keratomes may be combined with the invention to perform incisional maneuvers.

Accordingly, the scope of the invention should be determined not by the embodiments illustrated, but by the appended claims and their legal equivalents.

I claim:

1. A method for surgically correcting refractive errors, comprising the steps of:
    a. cutting a flap of corneal tissue;
    b. lifting and reflecting the flap to expose a posterior surface of the flap;
    c. positioning an anterior surface of the flap on a registration platen once the flap has been lifted and reflected;
    d. removing corneal tissue from the posterior surface of the flap using a femtosecond or picosecond pulse duration laser beam;
    e. compensating for involuntary motion of an eye during the corneal tissue removal step using an imaging eye tracking system;
    f. replacing the flap onto an exposed corneal bed; and
    g. supplying hydrating fluid during any or all of steps c-f to an anterior surface of the flap from below the flap using a plurality of hydrating features in communication with an upper surface of the registration platen, wherein the upper surface of the registration platen is in direct contact with the anterior surface of the flap, and
        wherein a position and an orientation of the flap is controlled by the registration platen.

2. The method of claim 1, wherein a position and an orientation of the flap is controlled by a registration platen, wherein the registration platen and the laser beam are configured to translate the position of the laser beam relative to the position of the posterior flap surface.

3. The method of claim 1, further comprising the step of controlling a z-position of the flap with respect to the laser beam by moving a registration platen and/or the laser beam to control a laser focus position.

4. The method of claim 1, wherein a position and an orientation of the flap is controlled by a registration platen that absorbs laser power that passes through the flap.

5. The method of claim 1, further comprising the step of supplying moisture to the posterior surface of the flap from above the flap using a plurality of hydration ports in communication with a lower surface of an aperture plate.

6. The method of claim 1, further comprising the step of directing a purge fluid onto the posterior surface of the flap from above the flap using one or more debris purge nozzles in communication with a lower surface of an aperture plate.

7. A method for surgically correcting refractive errors, comprising the steps of:
    a. cutting a flap of corneal tissue;
    b. lifting and reflecting the flap to expose a posterior surface of the flap;
    c. positioning an anterior surface of the flap on a registration platen;
    d. supplying hydrating fluid to the anterior surface of the flap from below the flap using a plurality of hydrating features in communication with an upper surface of the registration platen, wherein the upper surface of the registration platen is in direct contact with the anterior surface of the flap;
    e. removing corneal tissue from the posterior surface of the flap using a femtosecond or picosecond pulse duration laser beam; and
    f. replacing the flap onto an exposed corneal bed.

8. The method of claim 7, further comprising the step of compensating for involuntary motion of an eye during the corneal tissue removal step using an imaging eye tracking system.

9. The method of claim 7, wherein a position and an orientation of the flap is controlled by a registration platen, wherein the registration platen is repositionable relative to the laser beam, wherein the laser beam is configured to translate a position of the posterior flap surface.

10. The method of claim 7, further comprising the step of controlling a z-position of the flap with respect to the laser beam by moving the registration platen and/or the laser beam to control a laser focus position.

11. The method of claim 7, further comprising the step of supplying moisture to the posterior surface of the flap from above the flap using a plurality of hydration ports in communication with a lower surface of an aperture plate.

12. The method of claim 7, further comprising the step of directing a purge fluid onto the posterior surface of the flap from above the flap using one or more debris purge nozzles in communication with a lower surface of an aperture plate.

* * * * *